(12) United States Patent
Kaup et al.

(10) Patent No.: US 10,371,765 B2
(45) Date of Patent: Aug. 6, 2019

(54) GEOLOCATION OF MAGNETIC SOURCES USING VECTOR MAGNETOMETER SENSORS

(71) Applicant: Lockheed Martin Corporation, Bethesda, MD (US)

(72) Inventors: Peter G. Kaup, Marlton, NJ (US); Arul Manickam, Mount Laurel, NJ (US); John B. Stetson, New Hope, PA (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 302 days.

(21) Appl. No.: 15/437,222

(22) Filed: Feb. 20, 2017

(65) Prior Publication Data
US 2018/0011152 A1    Jan. 11, 2018

Related U.S. Application Data

(60) Provisional application No. 62/360,940, filed on Jul. 11, 2016.

(51) Int. Cl.
| | | |
|---|---|---|
| *G01R 33/26* | (2006.01) | |
| *G01C 21/20* | (2006.01) | |
| *G01R 33/32* | (2006.01) | |
| *G01N 24/12* | (2006.01) | |

(52) U.S. Cl.
CPC ............. *G01R 33/26* (2013.01); *G01C 21/20* (2013.01); *G01R 33/323* (2013.01); *G01N 24/12* (2013.01)

(58) Field of Classification Search
CPC ....... G01R 33/26; G01R 33/323; G01C 21/20
See application file for complete search history.

(56) References Cited

U.S. PATENT DOCUMENTS

| | | | |
|---|---|---|---|
| 2,746,027 | A | 5/1956 | Murray |
| 3,359,812 | A | 12/1967 | Everitt |
| 3,389,333 | A | 6/1968 | Wolff et al. |
| 3,490,032 | A | 1/1970 | Zurflueh |
| 3,514,723 | A | 5/1970 | Cutler |
| 3,518,531 | A | 6/1970 | Huggett |
| 3,621,380 | A | 11/1971 | Barlow, Jr. |

(Continued)

FOREIGN PATENT DOCUMENTS

| | | |
|---|---|---|
| CN | 105738845 A | 7/2016 |
| CN | 106257602 | 12/2016 |

(Continued)

OTHER PUBLICATIONS

Bui et al., "Noninvasive Fault Monitoring of Electrical Machines by Solving the Steady-State Magnetic Inverse Problem," in IEEE Transactions on Magnetics, vol. 44, No. 6, pp. 1050-1053, Jun. 24, 2008.

(Continued)

*Primary Examiner* — Dixomara Vargas
(74) *Attorney, Agent, or Firm* — Foley & Lardner LLP

(57) ABSTRACT

System and methods for determining an angle and/or geolocation of a dipole magnetic source relative to one or more DNV sensors. The system may include one or more DNV sensors, and a controller. The controller is configured to activate the DNV sensors, receive a set of vector measurements from the DNV sensors, and determine an angle of a magnetic source relative to the one or more DNV sensors based on the received set of vector measurements from the DNV sensors.

18 Claims, 4 Drawing Sheets

(56) References Cited

U.S. PATENT DOCUMENTS

| | | |
|---|---|---|
| 3,745,452 A | 7/1973 | Osburn et al. |
| 3,899,758 A | 8/1975 | Maier et al. |
| 4,025,873 A | 5/1977 | Chilluffo |
| 4,047,805 A | 9/1977 | Sekimura |
| 4,078,247 A | 3/1978 | Albrecht |
| 4,084,215 A | 4/1978 | Willenbrock |
| 4,322,769 A | 3/1982 | Cooper |
| 4,329,173 A | 5/1982 | Culling |
| 4,359,673 A | 11/1982 | Bross et al. |
| 4,368,430 A | 1/1983 | Dale et al. |
| 4,410,926 A | 10/1983 | Hafner et al. |
| 4,437,533 A | 3/1984 | Bierkarre et al. |
| 4,514,083 A | 4/1985 | Fukuoka |
| 4,588,993 A | 5/1986 | Babij et al. |
| 4,636,612 A | 1/1987 | Cullen |
| 4,638,324 A | 1/1987 | Hannan |
| 4,675,522 A | 6/1987 | Arunkumar |
| 4,768,962 A | 9/1988 | Kupfer et al. |
| 4,818,990 A | 4/1989 | Fernandes |
| 4,820,986 A | 4/1989 | Mansfield et al. |
| 4,945,305 A | 7/1990 | Blood |
| 4,958,328 A | 9/1990 | Stubblefield |
| 4,982,158 A | 1/1991 | Nakata et al. |
| 5,019,721 A | 5/1991 | Martens et al. |
| 5,038,103 A | 8/1991 | Scarzello et al. |
| 5,113,136 A | 5/1992 | Hayashi et al. |
| 5,134,369 A | 7/1992 | Lo et al. |
| 5,189,368 A | 2/1993 | Chase |
| 5,200,855 A | 4/1993 | Meredith et al. |
| 5,210,650 A | 5/1993 | O'Brien et al. |
| 5,245,347 A | 9/1993 | Bonta et al. |
| 5,252,912 A | 10/1993 | Merritt et al. |
| 5,301,096 A | 4/1994 | Klontz et al. |
| 5,384,109 A | 1/1995 | Klaveness et al. |
| 5,396,802 A | 3/1995 | Moss |
| 5,420,549 A | 5/1995 | Prestage |
| 5,425,179 A | 6/1995 | Nickel et al. |
| 5,427,915 A | 6/1995 | Ribi et al. |
| 5,548,279 A | 8/1996 | Gaines |
| 5,568,516 A | 10/1996 | Strohallen et al. |
| 5,586,069 A | 12/1996 | Dockser |
| 5,597,762 A | 1/1997 | Popovici et al. |
| 5,638,472 A | 6/1997 | Van Delden |
| 5,694,375 A | 12/1997 | Woodall |
| 5,719,497 A | 2/1998 | Veeser et al. |
| 5,731,996 A | 3/1998 | Gilbert |
| 5,764,061 A | 6/1998 | Asakawa et al. |
| 5,818,352 A | 10/1998 | McClure |
| 5,846,708 A | 12/1998 | Hollis et al. |
| 5,888,925 A | 3/1999 | Smith et al. |
| 5,894,220 A | 4/1999 | Wellstood et al. |
| 5,907,420 A | 5/1999 | Chraplyvy et al. |
| 5,907,907 A | 6/1999 | Ohtomo et al. |
| 5,915,061 A | 6/1999 | Vanoli |
| 5,995,696 A | 11/1999 | Miyagi et al. |
| 6,042,249 A | 3/2000 | Spangenberg |
| 6,057,684 A | 5/2000 | Murakami et al. |
| 6,064,210 A | 5/2000 | Sinclair |
| 6,121,053 A | 9/2000 | Kolber et al. |
| 6,124,862 A | 9/2000 | Boyken et al. |
| 6,130,753 A | 10/2000 | Hopkins et al. |
| 6,144,204 A | 11/2000 | Sementchenko |
| 6,195,231 B1 | 2/2001 | Sedlmayr et al. |
| 6,215,303 B1 | 4/2001 | Weinstock et al. |
| 6,262,574 B1 | 7/2001 | Cho et al. |
| 6,360,173 B1 | 3/2002 | Fullerton |
| 6,398,155 B1 | 6/2002 | Hepner et al. |
| 6,433,944 B1 | 8/2002 | Nagao et al. |
| 6,437,563 B1 | 8/2002 | Simmonds et al. |
| 6,472,651 B1 | 10/2002 | Ukai |
| 6,472,869 B1 | 10/2002 | Upschulte et al. |
| 6,504,365 B2 | 1/2003 | Kitamura |
| 6,518,747 B2 | 2/2003 | Sager et al. |
| 6,542,242 B1 | 4/2003 | Yost et al. |
| 6,621,377 B2 | 9/2003 | Osadchy et al. |
| 6,621,578 B1 | 9/2003 | Mizoguchi |
| 6,636,146 B1 | 10/2003 | Wehoski |
| 6,686,696 B2 | 2/2004 | Mearini et al. |
| 6,690,162 B1 | 2/2004 | Schopohl et al. |
| 6,765,487 B1 | 7/2004 | Holmes et al. |
| 6,788,722 B1 | 9/2004 | Kennedy et al. |
| 6,809,829 B1 | 10/2004 | Takata et al. |
| 7,118,657 B2 | 10/2006 | Golovchenko et al. |
| 7,221,164 B1 | 5/2007 | Barringer |
| 7,277,161 B2 | 10/2007 | Claus |
| 7,305,869 B1 | 12/2007 | Berman et al. |
| 7,307,416 B2 | 12/2007 | Islam et al. |
| 7,342,399 B1 | 3/2008 | Wiegert |
| RE40,343 E | 5/2008 | Anderson |
| 7,400,142 B2 | 7/2008 | Greelish |
| 7,413,011 B1 | 8/2008 | Chee et al. |
| 7,427,525 B2 | 9/2008 | Santori et al. |
| 7,448,548 B1 | 11/2008 | Compton |
| 7,471,805 B2 | 12/2008 | Goldberg |
| 7,474,090 B2 | 1/2009 | Islam et al. |
| 7,543,780 B1 | 6/2009 | Marshall et al. |
| 7,546,000 B2 | 6/2009 | Spillane et al. |
| 7,570,050 B2 | 8/2009 | Sugiura |
| 7,608,820 B1 | 10/2009 | Berman et al. |
| 7,705,599 B2 | 4/2010 | Strack et al. |
| 7,741,936 B1 | 6/2010 | Weller et al. |
| 7,805,030 B2 | 9/2010 | Bratkovski et al. |
| 7,868,702 B2 | 1/2011 | Ohnishi |
| 7,889,484 B2 | 2/2011 | Choi |
| 7,916,489 B2 | 3/2011 | Okuya |
| 7,932,718 B1 | 4/2011 | Wiegert |
| 7,983,812 B2 | 7/2011 | Potter |
| 8,022,693 B2 | 9/2011 | Meyersweissflog |
| 8,120,351 B2 | 2/2012 | Rettig et al. |
| 8,120,355 B1 | 2/2012 | Stetson |
| 8,124,296 B1 | 2/2012 | Fischel |
| 8,138,756 B2 | 3/2012 | Barclay et al. |
| 8,193,808 B2 | 6/2012 | Fu et al. |
| 8,294,306 B2 | 10/2012 | Kumar et al. |
| 8,310,251 B2 | 11/2012 | Orazem |
| 8,311,767 B1 | 11/2012 | Stetson |
| 8,334,690 B2 | 12/2012 | Kitching et al. |
| 8,415,640 B2 | 4/2013 | Babinec et al. |
| 8,471,137 B2 | 6/2013 | Adair et al. |
| 8,480,653 B2 | 7/2013 | Birchard et al. |
| 8,525,516 B2 | 9/2013 | Le Prado et al. |
| 8,547,090 B2 | 10/2013 | Lukin et al. |
| 8,574,536 B2 | 11/2013 | Boudou et al. |
| 8,575,929 B1 | 11/2013 | Wiegert |
| 8,686,377 B2 | 4/2014 | Twitchen et al. |
| 8,704,546 B2 | 4/2014 | Konstantinov |
| 8,758,509 B2 | 6/2014 | Twitchen et al. |
| 8,803,513 B2 | 8/2014 | Hosek et al. |
| 8,854,839 B2 | 10/2014 | Cheng et al. |
| 8,885,301 B1 | 11/2014 | Heidmann |
| 8,913,900 B2 | 12/2014 | Lukin et al. |
| 8,933,594 B2 | 1/2015 | Kurs |
| 8,947,080 B2 | 2/2015 | Lukin et al. |
| 8,963,488 B2 | 2/2015 | Campanella et al. |
| 9,103,873 B1 | 8/2015 | Martens et al. |
| 9,157,859 B2 | 10/2015 | Walsworth et al. |
| 9,245,551 B2 | 1/2016 | El Hallak et al. |
| 9,249,526 B2 | 1/2016 | Twitchen et al. |
| 9,270,387 B2 | 2/2016 | Wolfe et al. |
| 9,291,508 B1 | 3/2016 | Biedermann et al. |
| 9,317,811 B2 | 4/2016 | Scarsbrook |
| 9,369,182 B2 | 6/2016 | Kurs et al. |
| 9,442,205 B2 | 9/2016 | Geiser et al. |
| 9,541,610 B2 | 1/2017 | Kaup et al. |
| 9,551,763 B1 | 1/2017 | Hahn et al. |
| 9,557,391 B2 | 1/2017 | Egan et al. |
| 9,570,793 B2 | 2/2017 | Borodulin |
| 9,590,601 B2 | 3/2017 | Krause et al. |
| 9,614,589 B1 | 4/2017 | Russo et al. |
| 9,632,045 B2 | 4/2017 | Englund et al. |
| 9,645,223 B2 | 5/2017 | Megdal et al. |
| 9,680,338 B2 | 6/2017 | Malpas et al. |
| 9,689,679 B2 | 6/2017 | Budker et al. |
| 9,720,055 B1 | 8/2017 | Hahn et al. |

(56) References Cited

U.S. PATENT DOCUMENTS

| | | |
|---|---|---|
| 9,778,329 B2 | 10/2017 | Heidmann |
| 9,779,769 B2 | 10/2017 | Heidmann |
| 9,891,297 B2 | 2/2018 | Sushkov et al. |
| 2002/0144093 A1 | 10/2002 | Inoue et al. |
| 2002/0167306 A1 | 11/2002 | Zalunardo et al. |
| 2003/0058346 A1 | 3/2003 | Bechtel et al. |
| 2003/0076229 A1 | 4/2003 | Blanpain et al. |
| 2003/0094942 A1 | 5/2003 | Friend et al. |
| 2003/0098455 A1 | 5/2003 | Amin et al. |
| 2003/0235136 A1 | 12/2003 | Akselrod et al. |
| 2004/0013180 A1 | 1/2004 | Giannakis et al. |
| 2004/0022179 A1 | 2/2004 | Giannakis et al. |
| 2004/0042150 A1 | 3/2004 | Swinbanks et al. |
| 2004/0081033 A1 | 4/2004 | Arieli et al. |
| 2004/0095133 A1 | 5/2004 | Nikitin et al. |
| 2004/0109328 A1 | 6/2004 | Dahl et al. |
| 2004/0247145 A1 | 12/2004 | Luo et al. |
| 2005/0031840 A1 | 2/2005 | Swift et al. |
| 2005/0068249 A1 | 3/2005 | Frederick Du Toit et al. |
| 2005/0099177 A1 | 5/2005 | Greelish |
| 2005/0112594 A1 | 5/2005 | Grossman |
| 2005/0126905 A1 | 6/2005 | Golovchenko et al. |
| 2005/0130601 A1 | 6/2005 | Palermo et al. |
| 2005/0134257 A1 | 6/2005 | Etherington et al. |
| 2005/0138330 A1 | 6/2005 | Owens et al. |
| 2005/0146327 A1 | 7/2005 | Jakab |
| 2006/0012385 A1 | 1/2006 | Tsao et al. |
| 2006/0054789 A1 | 3/2006 | Miyamoto et al. |
| 2006/0055584 A1 | 3/2006 | Waite et al. |
| 2006/0062084 A1 | 3/2006 | Drew |
| 2006/0071709 A1 | 4/2006 | Maloberti et al. |
| 2006/0245078 A1 | 11/2006 | Kawamura |
| 2006/0247847 A1 | 11/2006 | Carter et al. |
| 2006/0255801 A1 | 11/2006 | Ikeda |
| 2006/0291771 A1 | 12/2006 | Braunisch et al. |
| 2007/0004371 A1 | 1/2007 | Okanobu |
| 2007/0120563 A1 | 5/2007 | Kawabata et al. |
| 2007/0247147 A1 | 10/2007 | Xiang et al. |
| 2007/0273877 A1 | 11/2007 | Kawano et al. |
| 2008/0016677 A1 | 1/2008 | Creighton, IV |
| 2008/0048640 A1 | 2/2008 | Hull et al. |
| 2008/0078233 A1 | 4/2008 | Larson et al. |
| 2008/0089367 A1 | 4/2008 | Srinivasan et al. |
| 2008/0204004 A1 | 8/2008 | Anderson |
| 2008/0217516 A1 | 9/2008 | Suzuki et al. |
| 2008/0239265 A1 | 10/2008 | Den Boef |
| 2008/0253264 A1 | 10/2008 | Nagatomi et al. |
| 2008/0265895 A1 | 10/2008 | Strack et al. |
| 2008/0266050 A1 | 10/2008 | Crouse et al. |
| 2008/0279047 A1 | 11/2008 | An et al. |
| 2008/0299904 A1 | 12/2008 | Yi et al. |
| 2009/0001979 A1 | 1/2009 | Kawabata |
| 2009/0015262 A1 | 1/2009 | Strack et al. |
| 2009/0042592 A1 | 2/2009 | Cho et al. |
| 2009/0058697 A1 | 3/2009 | Aas et al. |
| 2009/0060790 A1 | 3/2009 | Okaguchi et al. |
| 2009/0079417 A1 | 3/2009 | Mort et al. |
| 2009/0079426 A1 | 3/2009 | Anderson |
| 2009/0132100 A1 | 5/2009 | Shibata |
| 2009/0157331 A1 | 6/2009 | Van Netten |
| 2009/0161264 A1 | 6/2009 | Meyersweissflog |
| 2009/0195244 A1 | 8/2009 | Mouget et al. |
| 2009/0222208 A1 | 9/2009 | Speck |
| 2009/0243616 A1 | 10/2009 | Loehken et al. |
| 2009/0244857 A1 | 10/2009 | Tanaka |
| 2009/0277702 A1 | 11/2009 | Kanada et al. |
| 2009/0310650 A1 | 12/2009 | Chester et al. |
| 2010/0004802 A1 | 1/2010 | Bodin et al. |
| 2010/0015438 A1 | 1/2010 | Williams et al. |
| 2010/0015918 A1 | 1/2010 | Liu et al. |
| 2010/0045269 A1 | 2/2010 | Lafranchise et al. |
| 2010/0071904 A1 | 3/2010 | Burns et al. |
| 2010/0102809 A1 | 4/2010 | May |
| 2010/0102820 A1 | 4/2010 | Martinez et al. |
| 2010/0134922 A1 | 6/2010 | Yamada et al. |
| 2010/0157305 A1 | 6/2010 | Henderson |
| 2010/0188081 A1 | 7/2010 | Lammegger |
| 2010/0237149 A1 | 9/2010 | Olmstead |
| 2010/0271016 A1 | 10/2010 | Barclay et al. |
| 2010/0271032 A1 | 10/2010 | Helwig |
| 2010/0277121 A1 | 11/2010 | Hall et al. |
| 2010/0308813 A1 | 12/2010 | Lukin et al. |
| 2010/0315079 A1 | 12/2010 | Lukin et al. |
| 2010/0321117 A1 | 12/2010 | Gan |
| 2010/0326042 A1 | 12/2010 | McLean et al. |
| 2011/0031969 A1 | 2/2011 | Kitching et al. |
| 2011/0034393 A1 | 2/2011 | Justen et al. |
| 2011/0059704 A1 | 3/2011 | Norimatsu et al. |
| 2011/0062957 A1 | 3/2011 | Fu et al. |
| 2011/0062967 A1 | 3/2011 | Mohaupt |
| 2011/0066379 A1 | 3/2011 | Mes |
| 2011/0120890 A1 | 5/2011 | MacPherson et al. |
| 2011/0127999 A1 | 6/2011 | Lott et al. |
| 2011/0165862 A1 | 7/2011 | Yu et al. |
| 2011/0175604 A1 | 7/2011 | Polzer et al. |
| 2011/0176563 A1 | 7/2011 | Friel et al. |
| 2011/0243267 A1 | 10/2011 | Won et al. |
| 2011/0270078 A1 | 11/2011 | Wagenaar et al. |
| 2011/0279120 A1 | 11/2011 | Sudow et al. |
| 2011/0315988 A1 | 12/2011 | Yu et al. |
| 2012/0016538 A1 | 1/2012 | Waite et al. |
| 2012/0019242 A1 | 1/2012 | Hollenberg et al. |
| 2012/0037803 A1 | 2/2012 | Strickland |
| 2012/0044014 A1 | 2/2012 | Stratakos et al. |
| 2012/0051996 A1 | 3/2012 | Scarsbrook et al. |
| 2012/0063505 A1 | 3/2012 | Okamura et al. |
| 2012/0087449 A1 | 4/2012 | Ling et al. |
| 2012/0089299 A1 | 4/2012 | Breed |
| 2012/0140219 A1 | 6/2012 | Cleary |
| 2012/0181020 A1 | 7/2012 | Barron et al. |
| 2012/0194068 A1 | 8/2012 | Cheng et al. |
| 2012/0203086 A1 | 8/2012 | Rorabaugh et al. |
| 2012/0232838 A1 | 9/2012 | Kemppi et al. |
| 2012/0235633 A1 | 9/2012 | Kesler et al. |
| 2012/0235634 A1 | 9/2012 | Hall et al. |
| 2012/0245885 A1 | 9/2012 | Kimishima |
| 2012/0257683 A1 | 10/2012 | Schwager et al. |
| 2012/0281843 A1 | 11/2012 | Christensen et al. |
| 2012/0326793 A1 | 12/2012 | Gan |
| 2013/0043863 A1 | 2/2013 | Ausserlechner et al. |
| 2013/0070252 A1 | 3/2013 | Feth |
| 2013/0093424 A1 | 4/2013 | Blank et al. |
| 2013/0107253 A1 | 5/2013 | Santori |
| 2013/0127518 A1 | 5/2013 | Nakao |
| 2013/0179074 A1 | 7/2013 | Haverinen |
| 2013/0215712 A1 | 8/2013 | Geiser et al. |
| 2013/0223805 A1 | 8/2013 | Ouyang et al. |
| 2013/0265042 A1 | 10/2013 | Kawabata et al. |
| 2013/0265782 A1 | 10/2013 | Barrena et al. |
| 2013/0270991 A1 | 10/2013 | Twitchen et al. |
| 2013/0279319 A1 | 10/2013 | Matozaki et al. |
| 2013/0292472 A1 | 11/2013 | Guha |
| 2014/0012505 A1 | 1/2014 | Smith et al. |
| 2014/0015522 A1 | 1/2014 | Widmer et al. |
| 2014/0037932 A1 | 2/2014 | Twitchen et al. |
| 2014/0044208 A1 | 2/2014 | Woodsum |
| 2014/0061510 A1 | 3/2014 | Twitchen et al. |
| 2014/0070622 A1 | 3/2014 | Keeling et al. |
| 2014/0072008 A1 | 3/2014 | Faraon et al. |
| 2014/0077231 A1 | 3/2014 | Twitchen et al. |
| 2014/0081592 A1 | 3/2014 | Bellusci et al. |
| 2014/0104008 A1 | 4/2014 | Gan |
| 2014/0126334 A1 | 5/2014 | Megdal et al. |
| 2014/0139322 A1 | 5/2014 | Wang et al. |
| 2014/0153363 A1 | 6/2014 | Juhasz et al. |
| 2014/0154792 A1 | 6/2014 | Moynihan et al. |
| 2014/0159652 A1 | 6/2014 | Hall et al. |
| 2014/0166904 A1 | 6/2014 | Walsworth et al. |
| 2014/0167759 A1 | 6/2014 | Pines et al. |
| 2014/0168174 A1 | 6/2014 | Idzik et al. |
| 2014/0180627 A1 | 6/2014 | Naguib et al. |
| 2014/0191139 A1 | 7/2014 | Englund |
| 2014/0191752 A1 | 7/2014 | Walsworth et al. |
| 2014/0197831 A1 | 7/2014 | Walsworth |

(56) References Cited

U.S. PATENT DOCUMENTS

| | | |
|---|---|---|
| 2014/0198463 A1 | 7/2014 | Klein |
| 2014/0210473 A1 | 7/2014 | Campbell et al. |
| 2014/0215985 A1 | 8/2014 | Pollklas |
| 2014/0225606 A1 | 8/2014 | Endo et al. |
| 2014/0247094 A1 | 9/2014 | Englund et al. |
| 2014/0264723 A1 | 9/2014 | Liang et al. |
| 2014/0265555 A1 | 9/2014 | Hall et al. |
| 2014/0272119 A1 | 9/2014 | Kushalappa et al. |
| 2014/0273826 A1 | 9/2014 | Want et al. |
| 2014/0291490 A1 | 10/2014 | Hanson et al. |
| 2014/0297067 A1 | 10/2014 | Malay |
| 2014/0306707 A1 | 10/2014 | Walsworth et al. |
| 2014/0327439 A1 | 11/2014 | Cappellaro et al. |
| 2014/0335339 A1 | 11/2014 | Dhillon et al. |
| 2014/0340085 A1 | 11/2014 | Cappellaro et al. |
| 2014/0368191 A1 | 12/2014 | Goroshevskiy et al. |
| 2015/0001422 A1 | 1/2015 | Englund et al. |
| 2015/0009746 A1 | 1/2015 | Kucsko et al. |
| 2015/0015247 A1 | 1/2015 | Goodwill et al. |
| 2015/0018018 A1 | 1/2015 | Shen et al. |
| 2015/0022404 A1 | 1/2015 | Chen et al. |
| 2015/0048822 A1 | 2/2015 | Walsworth et al. |
| 2015/0054355 A1 | 2/2015 | Ben-Shalom et al. |
| 2015/0061590 A1 | 3/2015 | Widmer et al. |
| 2015/0061670 A1 | 3/2015 | Fordham et al. |
| 2015/0090033 A1 | 4/2015 | Budker et al. |
| 2015/0128431 A1 | 5/2015 | Kuo |
| 2015/0137793 A1 | 5/2015 | Englund et al. |
| 2015/0153151 A1 | 6/2015 | Kochanski |
| 2015/0192532 A1 | 7/2015 | Clevenson et al. |
| 2015/0192596 A1 | 7/2015 | Englund et al. |
| 2015/0225052 A1 | 8/2015 | Cordell |
| 2015/0235661 A1 | 8/2015 | Heidmann |
| 2015/0253355 A1 | 9/2015 | Grinolds et al. |
| 2015/0268373 A1 | 9/2015 | Meyer |
| 2015/0269957 A1 | 9/2015 | El Hallak et al. |
| 2015/0276897 A1 | 10/2015 | Leussler et al. |
| 2015/0288352 A1 | 10/2015 | Krause et al. |
| 2015/0299894 A1 | 10/2015 | Markham et al. |
| 2015/0303333 A1 | 10/2015 | Yu et al. |
| 2015/0314870 A1 | 11/2015 | Davies |
| 2015/0326030 A1 | 11/2015 | Malpas et al. |
| 2015/0326410 A1 | 11/2015 | Krause et al. |
| 2015/0354985 A1 | 12/2015 | Judkins et al. |
| 2015/0358026 A1 | 12/2015 | Gan |
| 2015/0374250 A1 | 12/2015 | Hatano et al. |
| 2015/0377865 A1 | 12/2015 | Acosta et al. |
| 2015/0377987 A1 | 12/2015 | Menon et al. |
| 2016/0018269 A1 | 1/2016 | Maurer et al. |
| 2016/0031339 A1 | 2/2016 | Geo |
| 2016/0036529 A1 | 2/2016 | Griffith et al. |
| 2016/0052789 A1 | 2/2016 | Gaathon et al. |
| 2016/0054402 A1 | 2/2016 | Meriles |
| 2016/0061914 A1 | 3/2016 | Jelezko |
| 2016/0071532 A9 | 3/2016 | Heidmann |
| 2016/0077167 A1 | 3/2016 | Heidmann |
| 2016/0097702 A1 | 4/2016 | Zhao et al. |
| 2016/0113507 A1 | 4/2016 | Reza et al. |
| 2016/0131723 A1 | 5/2016 | Nagasaka |
| 2016/0139048 A1 | 5/2016 | Heidmann |
| 2016/0146904 A1 | 5/2016 | Stetson, Jr. et al. |
| 2016/0161429 A1 | 6/2016 | Englund et al. |
| 2016/0161583 A1 | 6/2016 | Meriles et al. |
| 2016/0174867 A1 | 6/2016 | Hatano |
| 2016/0214714 A1 | 7/2016 | Sekelsky |
| 2016/0216304 A1 | 7/2016 | Sekelsky |
| 2016/0216340 A1 | 7/2016 | Egan et al. |
| 2016/0216341 A1 | 7/2016 | Boesch et al. |
| 2016/0221441 A1 | 8/2016 | Hall et al. |
| 2016/0223621 A1 | 8/2016 | Kaup et al. |
| 2016/0231394 A1 | 8/2016 | Manickam et al. |
| 2016/0266220 A1 | 9/2016 | Sushkov et al. |
| 2016/0282427 A1 | 9/2016 | Heidmann |
| 2016/0291191 A1 | 10/2016 | Fukushima et al. |
| 2016/0313408 A1 | 10/2016 | Hatano et al. |
| 2016/0348277 A1 | 12/2016 | Markham et al. |
| 2016/0356863 A1 | 12/2016 | Boesch et al. |
| 2017/0010214 A1 | 1/2017 | Osawa et al. |
| 2017/0010334 A1 | 1/2017 | Krause et al. |
| 2017/0010338 A1 | 1/2017 | Bayat et al. |
| 2017/0010594 A1 | 1/2017 | Kottapalli et al. |
| 2017/0023487 A1 | 1/2017 | Boesch |
| 2017/0030982 A1 | 2/2017 | Jeske et al. |
| 2017/0038314 A1 | 2/2017 | Suyama et al. |
| 2017/0038411 A1 | 2/2017 | Yacobi et al. |
| 2017/0068012 A1 | 3/2017 | Fisk |
| 2017/0074660 A1 | 3/2017 | Gann et al. |
| 2017/0075020 A1 | 3/2017 | Gann et al. |
| 2017/0075205 A1 | 3/2017 | Kriman et al. |
| 2017/0077665 A1 | 3/2017 | Liu et al. |
| 2017/0104426 A1 | 4/2017 | Mills |
| 2017/0138735 A1 | 5/2017 | Cappellaro et al. |
| 2017/0139017 A1 | 5/2017 | Egan et al. |
| 2017/0146615 A1 | 5/2017 | Wolf et al. |
| 2017/0199156 A1 | 7/2017 | Villani et al. |
| 2017/0205526 A1 | 7/2017 | Meyer |
| 2017/0207823 A1 | 7/2017 | Russo et al. |
| 2017/0211947 A1 | 7/2017 | Fisk |
| 2017/0212046 A1 | 7/2017 | Cammerata |
| 2017/0212177 A1 | 7/2017 | Coar et al. |
| 2017/0212178 A1 | 7/2017 | Hahn et al. |
| 2017/0212179 A1 | 7/2017 | Hahn et al. |
| 2017/0212180 A1 | 7/2017 | Hahn et al. |
| 2017/0212181 A1 | 7/2017 | Coar et al. |
| 2017/0212182 A1 | 7/2017 | Hahn et al. |
| 2017/0212183 A1 | 7/2017 | Egan et al. |
| 2017/0212184 A1 | 7/2017 | Coar et al. |
| 2017/0212185 A1 | 7/2017 | Hahn et al. |
| 2017/0212186 A1 | 7/2017 | Hahn et al. |
| 2017/0212187 A1 | 7/2017 | Hahn et al. |
| 2017/0212190 A1 | 7/2017 | Reynolds et al. |
| 2017/0212258 A1 | 7/2017 | Fisk |
| 2017/0261629 A1 | 9/2017 | Gunnarsson et al. |
| 2017/0343617 A1 | 11/2017 | Manickam et al. |
| 2017/0343619 A1 | 11/2017 | Manickam et al. |
| 2017/0343621 A1 | 11/2017 | Hahn et al. |
| 2017/0343695 A1 | 11/2017 | Stetson et al. |
| 2018/0136291 A1 | 5/2018 | Pham et al. |
| 2018/0275209 A1 | 9/2018 | Mandeville et al. |
| 2018/0275212 A1 | 9/2018 | Hahn et al. |

FOREIGN PATENT DOCUMENTS

| | | |
|---|---|---|
| DE | 69608006 T2 | 2/2001 |
| DE | 19600241 C2 | 8/2002 |
| DE | 10228536 A1 | 1/2003 |
| EP | 0 161 940 B1 | 12/1990 |
| EP | 0 718 642 | 6/1996 |
| EP | 0 726 458 | 8/1996 |
| EP | 1 505 627 | 2/2005 |
| EP | 1 685 597 | 8/2006 |
| EP | 1 990 313 | 11/2008 |
| EP | 2 163 392 | 3/2010 |
| EP | 2 495 166 A1 | 9/2012 |
| EP | 2 587 232 A1 | 5/2013 |
| EP | 2 705 179 | 3/2014 |
| EP | 2 707 523 | 3/2014 |
| EP | 2 745 360 | 6/2014 |
| EP | 2 769 417 | 8/2014 |
| EP | 2 790 031 | 10/2014 |
| EP | 2 837 930 A1 | 2/2015 |
| EP | 2 907 792 | 8/2015 |
| GB | 2 423 366 A | 8/2006 |
| GB | 2 433 737 | 7/2007 |
| GB | 2 482 596 | 2/2012 |
| GB | 2 483 767 | 3/2012 |
| GB | 2 486 794 | 6/2012 |
| GB | 2 490 589 | 11/2012 |
| GB | 2 491 936 | 12/2012 |
| GB | 2 493 236 | 1/2013 |
| GB | 2 495 632 A | 4/2013 |
| GB | 2 497 660 | 6/2013 |
| GB | 2 510 053 A | 7/2014 |
| GB | 2 515 226 | 12/2014 |

(56) References Cited

FOREIGN PATENT DOCUMENTS

| | | |
|---|---|---|
| GB | 2 522 309 | 7/2015 |
| GB | 2 526 639 | 12/2015 |
| JP | 3782147 B2 | 6/2006 |
| JP | 4800896 B2 | 10/2011 |
| JP | 2012-103171 | 5/2012 |
| JP | 2012-110489 | 6/2012 |
| JP | 2012-121748 | 6/2012 |
| JP | 2013-028497 | 2/2013 |
| JP | 5476206 B2 | 4/2014 |
| JP | 5522606 B2 | 6/2014 |
| JP | 5536056 B2 | 7/2014 |
| JP | 5601183 B2 | 10/2014 |
| JP | 2014-215985 | 11/2014 |
| JP | 2014-216596 | 11/2014 |
| JP | 2015-518562 A | 7/2015 |
| JP | 5764059 B2 | 8/2015 |
| JP | 2015-167176 | 9/2015 |
| JP | 2015-529328 | 10/2015 |
| JP | 5828036 B2 | 12/2015 |
| JP | 5831947 B2 | 12/2015 |
| WO | WO-87/04028 A1 | 7/1987 |
| WO | WO-88/04032 A1 | 6/1988 |
| WO | WO-95/33972 A1 | 12/1995 |
| WO | WO-2009/073736 | 6/2009 |
| WO | WO-2011/046403 A2 | 4/2011 |
| WO | WO-2011/153339 A1 | 12/2011 |
| WO | WO-2012/016977 A2 | 2/2012 |
| WO | WO-2012/084750 | 6/2012 |
| WO | WO-2013/027074 | 2/2013 |
| WO | WO-2013/059404 A1 | 4/2013 |
| WO | WO-2013/066446 A1 | 5/2013 |
| WO | WO-2013/066448 | 5/2013 |
| WO | WO-2013/093136 A1 | 6/2013 |
| WO | WO-2013/188732 A1 | 12/2013 |
| WO | WO-2013/190329 A1 | 12/2013 |
| WO | WO-2014/011286 A2 | 1/2014 |
| WO | WO-2014/099110 A2 | 6/2014 |
| WO | WO-2014/135544 A1 | 9/2014 |
| WO | WO-2014/135547 A1 | 9/2014 |
| WO | WO-2014/166883 A1 | 10/2014 |
| WO | WO-2014/210486 A1 | 12/2014 |
| WO | WO-2015/015172 A1 | 2/2015 |
| WO | WO-2015/142945 | 9/2015 |
| WO | WO-2015/157110 A1 | 10/2015 |
| WO | WO-2015/157290 A1 | 10/2015 |
| WO | WO-2015/158383 A1 | 10/2015 |
| WO | WO-2015/193156 A1 | 12/2015 |
| WO | WO-2016/075226 A1 | 5/2016 |
| WO | WO-2016/118756 A1 | 7/2016 |
| WO | WO-2016/118791 A1 | 7/2016 |
| WO | WO-2016/122965 A1 | 8/2016 |
| WO | WO-2016/122966 A1 | 8/2016 |
| WO | WO-2016/126435 A1 | 8/2016 |
| WO | WO-2016/126436 A1 | 8/2016 |
| WO | WO-2016/190909 A2 | 12/2016 |
| WO | WO-2017/007513 A1 | 1/2017 |
| WO | WO-2017/007514 A1 | 1/2017 |
| WO | WO-2017/014807 A1 | 1/2017 |
| WO | WO-2017/039747 A1 | 3/2017 |
| WO | WO-2017/095454 A1 | 6/2017 |
| WO | WO-2017/127079 A1 | 7/2017 |
| WO | WO-2017/127080 A1 | 7/2017 |
| WO | WO-2017/127081 A1 | 7/2017 |
| WO | WO-2017/127085 A1 | 7/2017 |
| WO | WO-2017/127090 A1 | 7/2017 |
| WO | WO-2017/127091 A1 | 7/2017 |
| WO | WO-2017/127093 A1 | 7/2017 |
| WO | WO-2017/127094 A1 | 7/2017 |
| WO | WO-2017/127095 A1 | 7/2017 |
| WO | WO-2017/127096 A1 | 7/2017 |
| WO | WO-2017/127097 A1 | 7/2017 |
| WO | WO-2017/127098 A1 | 7/2017 |

OTHER PUBLICATIONS

Chadebec et al., "Rotor fault detection of electrical machines by low frequency magnetic stray field analysis," 2005 5th IEEE International Symposium on Diagnostics for Electric Machines, Power Electronics and Drives, Vienna, 2005, submitted Mar. 22, 2006, pp. 1-6.

Froidurot et al., "Magnetic discretion of naval propulsion machines," in IEEE Transactions on Magnetics, vol. 38, No. 2, pp. 1185-1188, Mar. 2002.

IEEE Std 802.11 TM-2012 Wireless LAN Medium Access Control (MAC) and Physical Layer (PHY) Specifications, 1 page.

Kwon et al., "Analysis of the far field of permanent-magnet motors and effects of geometric asymmetries and unbalance in magnet design," in IEEE Transactions on Magnetics, vol. 40, No. 2, pp. 435-442, Mar. 2004.

Maertz et al., "Vector magnetic field microscopy using nitrogen vacancy centers in diamond", Applied Physics Letters 96, No. 9, Mar. 1, 2010, pp. 092504-1-092504-3.

U.S. Notice of Allowance dated Feb. 2, 2018, from related U.S. Appl. No. 15/003,292, 8 pages.

U.S. Notice of Allowance dated Feb. 21, 2018, from related U.S. Appl. No. 15/003,176, 9 pages.

U.S. Office Action dated Feb. 1, 2018, from related U.S. Appl. No. 15/003,577, 16 pages.

U.S. Office Action dated Feb. 5, 2018, from related U.S. Appl. No. 15/450,504, 12 pages.

U.S. Office Action dated Jan. 25, 2018, from related U.S. Appl. No. 15/672,953, 28 pages.

U.S. Office Action dated Jan. 26, 2018, from related U.S. Appl. No. 15/003,678, 14 pages.

U.S. Office Action dated Mar. 27, 2018, from related U.S. Appl. No. 15/468,386, 21 pages.

U.S. Office Action dated Mar. 28, 2018, from related U.S. Appl. No. 15/003,177, 12 pages.

U.S. Office Action dated Mar. 5, 2018, from related U.S. Appl. No. 14/866,730, 14 pages.

U.S. Office Action dated Mar. 8, 2018, from related U.S. Appl. No. 15/380,691, 12 pages.

U.S. Office Action dated Mar. 8, 2018, from related U.S. Appl. No. 15/479,256, 30 pages.

Wegerich, "Similarity based modeling of time synchronous averaged vibration signals for machinery health monitoring," 2004 IEEE Aerospace Conference Proceedings (IEEE Cat. No. 04TH8720), 2004, pp. 3654-3662 vol. 6.

Wikipedia, "Continuous phase modulation", downloaded from https://web.archive.org/web/20151017015236/https://en.wikipedia.org/wiki/Continuous_phase_modulation on May 10, 2017, 3 pages.

Wikipedia, "Minimum-shift keying", downloaded from https://web.archive.org/web/20151017175828/https://en.wikipedia.org/wiki/Minimum-shift_keying on May 10, 2017, 2 pages.

European Extended Search Report for Appl. Ser. No. 16743879.5 dated Sep. 11, 2018, 11 pages.

European Extended Search Report for Appl. Ser. No. 16800410.9 dated Oct. 12, 2018, 11 pages.

Niu, "Crack Detection of Power Line Based on Metal Magnetic Memory Non-destructive", TELKOMNIKA Indonesian Journal of Electrical Engineering, vol. 12, No. 11, Nov. 1, 2014, pp. 7764-7771.

U.S. Final Office Action for U.S. Appl. No. 15/380,691 dated Sep. 21, 2018, 12 pages.

U.S. Final Office Action for U.S. Appl. No. 15/479,256 dated Sep. 10, 2018, 20 pages.

U.S. Non-Final Office Action for U.S. Appl. No. 15/443,422 dated Oct. 2, 2018, 16 pages.

U.S. Non-Final Office Action for U.S. Appl. No. 15/446,373 dated Oct. 1, 2018, 13 pages.

U.S. Non-Final Office Action for U.S. Appl. No. 15/454,162 dated Sep. 10, 2018, 13 pages.

U.S. Non-Final Office Action for U.S. Appl. No. 15/468,282 dated Oct. 10, 2018, 12 pages.

U.S. Non-Final Office Action for U.S. Appl. No. 15/372,201 dated Oct. 15, 2018, 12 pages.

(56) References Cited

OTHER PUBLICATIONS

U.S. Non-Final Office Action for U.S. Appl. No. 15/468,274 dated Oct. 26, 2018, 11 pages.
U.S. Notice of Allowance for U.S. Appl. No. 14/866,730 dated Aug. 15, 2018, 9 pages.
U.S. Notice of Allowance for U.S. Appl. No. 15/468,289 dated Oct. 17, 2018, 12 pages.
U.S. Notice of Allowance for U.S. Appl. No. 15/003,704 dated Nov. 2, 2018, 19 pages.
U.S. Office Action for U.S. Appl. No. 15/468,397 dated Sep. 13, 2018, 7 pages.
U.S. Notice of Allowance dated Oct. 19, 2017, from related U.S. Appl. No. 15/179,957, 5 pages.
U.S. Notice of Allowance dated Oct. 23, 2017, from related U.S. Appl. No. 15/003,797, 6 pages.
U.S. Office Action dated Nov. 24, 2017, from related U.S. Appl. No. 15/003,145, 14 pages.
U.S. Office Action dated Nov. 27, 2017, from related U.S. Appl. No. 15/468,386, 28 pages.
"'Diamond Sensors, Detectors, and Quantum Devices' in Patent Application Approval Process," Chemicals & Chemistry, pp. 1-6, (Feb. 28, 2014), 6 pages.
"Findings from University of Stuttgart in physics reported," Science Letter, (Jul. 7, 2009), 2 pages.
"New Findings on Nitrogen from Ecole Normale Superieure Summarized (Magnetic imaging with an ensemble of nitrogen vacancy-centers in diamond)," Physics Week, pp. 1-2, (Jul. 21, 2015), 2 pages.
"Patent Issued for Diamond Sensors, Detectors, and Quantum Devices," Journal of Engineering, pp. 1-5 (Feb. 15, 2016), 5 pages.
"Researchers Submit Patent Application, 'Diamond Sensors, Detectors, and Quantum Devices', for Approval," Chemicals & Chemistry, pp. 1-7, (Apr. 11, 2014), 7 pages.
Acosta et al., "Broadband magnetometry by infrared-absorption detection of nitrogen-vacancy ensembles in diamond," Appl. Phys. Letters 97: 174104 (Oct. 29, 2010), 4 pages.
Acosta et al., "Diamonds with a high density of nitrogen-vacancy centers for magnetometry applications," Physical Review B 80(115202): 1-15 (Sep. 9, 2009), 15 pages.
Acosta et al., "Nitrogen-vacancy centers: physics and applications," MRS Bulletin 38(2): 127-130 (Feb. 2013), 4 pages.
Acosta, "Optical Magnetometry with Nitrogen-Vacancy Centers in Diamond," University of California Berkeley, (Spring 2011), 118 pages.
Aiello et al., "Composite-pulse magnetometry with a solid-state quantum sensor," Nature Communications 4(1419): 1-6 (Jan. 29, 2013), 6 pages.
Alam, "Solid-state 13C magic angle spinning NMR spectroscopy characterization of particle size structural variations in synthetic nanodiamonds," Materials Chemistry and Physics 85(2-3): 310-315 (Jun. 15, 2004), 6 pages.
Albrecht et al., "Coupling of nitrogen vacancy centres in nanodiamonds by means of phonons," New Journal of Physics 15(083014): 1-26 (Aug. 6, 2013), 27 pages.
Appel et al., "Nanoscale microwave imaging with a single electron spin in diamond," New Journal of Physics 17(112001): 1-6 (Nov. 3, 2015), 7 pages.
Arai et al., "Fourier magnetic imaging with nanoscale resolution and compressed sensing speed-up using electronic spins in diamond," Nature Nanotechnology 10: 859-864 (Aug. 10, 2015), 7 pages.
Aslam et al., "Single spin optically detected magnetic resonance with 60-90 GHz (E-band) microwave resonators," Review of Scientific Instruments 86(064704): 1-8 (Jun. 22, 2015), 9 pages.
Awschalom et al., "Diamond age of spintronics," Scientific American 297: 84-91 (Oct. 2007), 8 pages.
Babamoradi et al., "Correlation between entanglement and spin density in nitrogen-vacancy center of diamond," European Physical Journal D 65: 597-603 (Dec. 1, 2011), 7 pages.

Babunts et al., "Diagnostics of NV defect structure orientation in diamond using optically detected magnetic resonance with a modulated magnetic field," Technical Physics Letters 41(6): 583-586 (Jun. 2015; first published online Jul. 14, 2015), 4 pages.
Babunts et al., "Temperature-scanned magnetic resonance and the evidence of two-way transfer of a nitrogen nuclear spin hyperfine interaction in coupled NV-N pairs in diamond," JETP Letters 95(8): 429-432 (Jun. 27, 2012), 4 pages.
Bagguley et al., "Zeeman effect of acceptor states in semiconducting diamond," Journal of the Physical Society of Japan 21(Supplement): 244-248 (1966), 7 pages.
Balasubramanian et al., "Nanoscale imaging magnetometry with diamond spins under ambient conditions," Nature 455: 648-651 (Oct. 2, 2008), 5 pages.
Balmer et al., "Chemical Vapour deposition synthetic diamond: materials technology and applications," J. of Physics: Condensed Matter 21(36): 1-51 (Aug. 19, 2009), 51 pages.
Baranov et al., "Enormously High Concentrations of Fluorescent Nitrogen-Vacancy Centers Fabricated by Sintering of Detonation Nanodiamonds," Small 7(11): 1533-1537 (Jun. 6, 2011; first published online Apr. 26, 2011), 5 pages.
Barfuss et al., "Strong mechanical driving of a single electron spin," Nature Physics 11: 820-824 (Aug. 3, 2015), 6 pages.
Barry et al., "Optical magnetic detection of single-neuron action potentials using quantum defects in diamond," as submitted to Quantum Physics on Feb. 2, 2016, 23 pages.
Bennett et al., "CVD Diamond for High Power Laser Applications," SPIE 8603, High-Power Laser Materials Processing: Lasers, Beam Delivery, Diagnostics, and Applications II, 860307 (Feb. 22, 2013), 10 pages.
Berman & Chernobrod, "Single-spin microscope with subnanoscale resolution based on optically detected magnetic resonance," SPIE 7608, Quantum Sensing and Nanophotonic Devices VII, 76080Y (Jan. 23, 2010), 4 pages.
Berman et al. "Measurement of single electron and nuclear spin states based on optically detected magnetic resonance," J. Physics: Conf. Series 38: 167-170 (2006), 5 pages.
Blakley et al., "Room-temperature magnetic gradiometry with fiber-coupled nitrogen-vacancy centers in diamond," Optics Letters 40(16): 3727-3730 (Aug. 5, 2015), 4 pages.
Bourgeois, et al., "Photoelectric detection of electron spin resonance of nitrogen-vacancy centres in diamond," Nature Communications 6(8577): 1-8 (Oct. 21, 2015), 8 pages.
Brenneis, et al. "Ultrafast electronic readout of diamond nitrogen-vacancy centres coupled to graphene." Nature nanotechnology 10.2 (2015): 135-139.
Bucher et al, "High Resolution Magnetic Resonance Spectroscopy Using Solid-State Spins", May 25, 2017, downloaded from https://arxiv.org/ (arXiv.org > quant-ph > arXiv:1705.08887) on May 25, 2017, pp. 1-24.
Budker & Kimball, "Optical Magnetometry," Cambridge Press, (2013), 11 pages.
Budker & Romalis, "Optical Magnetometry," Nature Physics 3: 227-243 (Apr. 2007), 8 pages.
Casanova, et al., "Effect of magnetic field on phosphorus centre in diamond," Physica Status Solidi A 186(2): 291-295 (Jul. 30, 2001), 6 pages.
Castelletto, et al., "Frontiers in diffraction unlimited optical methods for spin manipulation, magnetic field sensing and imaging using diamond nitrogen vacancy defects," Nanophotonics 1(2): 139-153 (Nov. 2012), 15 pages.
Chapman, et al., "Anomalous saturation effects due to optical spin depolarization in nitrogen-vacancy centers in diamond nanocrystals," Physical Review B 86(045204): 1-8 (Jul. 10, 2012), 8 pages.
Chavez, et al. "Detecting Arctic oil spills with NMR: a feasibility study." Near Surface Geophysics 13.4 (Feb. 2015): 409-416.
Chen et al., "Vector magnetic field sensing by a single nitrogen vacancy center in diamond," EPL 101(67003): 1-5 (Mar. 2013), 6 pages.
Chernobrod et al., "Improving the sensitivity of frequency modulation spectroscopy using nanomechanical cantilevers," Applied Physics Letters 85(17): 3896-3898 (Oct. 25, 2004), 3 pages.

(56) References Cited

OTHER PUBLICATIONS

Chernobrod et al., "Spin Microscope Based on Optically Detected Magnetic Resoncance," Journal of Applied Physics 97(014903): 1-3, (2005; first published online Dec. 10, 2004), 4 pages.
Childress et al., "Coherent dynamics of coupled electron and nuclear spin qubits in diamond," Science 314(5797): 281-285 (Oct. 13, 2006), 6 pages.
Chipaux et al., "Magnetic imaging with an ensemble of nitrogen vacancy-centers in diamond," European Physical Journal D 69(166): 1-10 (Jul. 2, 2015), 10 pages.
Chipaux et al., "Nitrogen vacancies (NV) centers in diamond for magnetic sensors and quantum sensing," SPIE 9370, Quantum Sensing and Nanophotonic Devices XII, 93701V (Feb. 8, 2015), 6 pages.
Chipaux, et al., "Wide bandwidth instantaneous radio frequency spectrum analyzer based on nitrogen vacancy centers in diamond," Applied Physics Letters 107(233502): 1-5 (2015), 6 pages.
Clevenson et al., "Broadband magnetometry and temperature sensing with a light-trapping diamond waveguide," Nature Physics 11: 393-397 (May 2015; first published online Apr. 6, 2015), 6 pages.
Constable, "Geomagnetic Spectrum, Temporal." in Encyclopedia of Geomagnetism and Paleomagnetism, pp. 353-355, Springer: Dordrecht, Netherlands (2007), 3 pages.
Cooper et al., "Time-resolved magnetic sensing with electronic spins in diamond," Nature Communications 5:3141: 1-7 (Jan. 24, 2014), 7 pages.
Creedon et al., "Strong coupling between P1 diamond impurity centers and a three-dimensional lumped photonic microwave cavity," Physical Review B 91(140408R): 1-5 (Apr. 24, 2015), 5 pages.
Dale, et al. "Medical applications of diamond magnetometry: commercial viability." arXiv preprint arXiv:1705.01994 (May 8, 2017), pp. 1-7.
Davies, "Current problems in diamond: towards a quantitative understanding," Physica B 273-274: 15-13 (Dec. 15, 1999), 9 pages.
De Lange et al., "Single-Spin Magnetometry with Multipulse Sensing Sequences," Physical Review Letters 106(080802): 1-4 (Feb. 24, 2011), 4 pages.
Degen, "Scanning magnetic field microscope with a diamond single-spin sensor," Applied Physics Letters 92(243111): 1-3 (Jun. 17, 2008), 3 pages.
Delacroix et al., "Design, manufacturing, and performance analysis of mid-infrared achromatic half-wave plates with diamond subwavelength gratings," Applied Optics 51(24): 5897-5902 (Aug. 16, 2012), 6 pages.
Denatale et al., "Fabrication and characterization of diamond moth eye antireflective surfaces on Ge," J. of Applied Physics 71: 1388-1393 (Mar. 1992), 8 pages.
Dobrovitski et al., "Quantum Control over Single Spins in Diamond," Annual Review of Condensed Matter Physics 4: 23-50 (Apr. 2013), 30 pages.
Doherty et al., "The nitrogen-vacancy colour centre in diamond," Physics Reports 528: 1-45 (Jul. 1, 2013), 45 pages.
Doherty et al., "Theory of the ground-state spin of the NV—center in diamond," Physical Review B 85(205203): 1-21 (May 3, 2012), 21 pages.
Doi et al., "Pure negatively charged state of the NV center in n-type diamond," Physical Review B 93(081203): 1-6 (Feb. 3, 2016), 6 pages.
Drake et al., "Influence of magnetic field alignment and defect concentration on nitrogen-vacancy polarization in diamond," New Journal of Physics 18(013011): 1-8 (Jan. 2016; first published on Dec. 24, 2015), 9 pages.
Dreau et al., "Avoiding power broadening in optically detected magnetic resonance of single NV defects for enhanced dc magnetic field sensitivity," Physical Review B 84(195204): 1-8 (Nov. 23, 2011), 8 pages.
Dreau et al., "High-resolution spectroscopy of single NV defects coupled with nearby 13C nuclear spins in diamond," Physical Review B 85(134107): 1-7 (Apr. 20, 2012), 7 pages.
Dumeige et al., "Magnetometry with nitrogen-vacancy ensembles in diamond based on infrared absorption in a doubly resonant optical cavity," Physical Review B 87(155202): 1-9 (Apr. 8, 2013), 9 pages.
Epstein et al., "Anisotropic interactions of a single spin and dark-spin spectroscopy in diamond," Nature Physics 1:94-98 (Nov. 2005), 5 pages.
Fallah et al., "Multi-sensor approach in vessel magnetic wake imaging," Wave Motion 51(1): 60-76 (Jan. 2014), retrieved from http://www.sciencedirect.com/science/article/pii/S0165212513001133 (Aug. 21, 2016).
Fedotov et al., "High-resolution magnetic field imaging with a nitrogen-vacancy diamond sensor integrated with a photonic-crystal fiber," Optics Letters 41(3): 472-475 (Feb. 1, 2016; published Jan. 25, 2016), 4 pages.
Fedotov et al., "Photonic-crystal-fiber-coupled photoluminescence interrogation of nitrogen vacancies in diamond nanoparticles," Laser Physics Letters 9(2): 151-154 (Feb. 2012; first published online Dec. 2, 2011), 5 pages.
Feng & Wei, "A steady-state spectral method to fit microwave absorptions of NV centers in diamonds: application to sensitive magnetic field sensing," Measurement Science & Technology 25(105102): 1-6 (Oct. 2014; first published online Aug. 29, 2014), 7 pages.
Fologea, et al. "Detecting single stranded DNA with a solid state nanopore." Nano Letters 5.10 (Aug. 15, 2005): 1905-1909.
Freitas, et al., "Solid-State Nuclear Magnetic Resonance (NMR) Methods Applied to the Study of Carbon Materials," Chemistry and Physics of Carbon, vol. 31 (2012), 45 pages.
Gaebel, et al. "Room-temperature coherent coupling of single spins in diamond." Nature Physics 2.6 (May 28, 2006): 408-413.
GB Examination Report from United Kingdom application No. GB 1618202.4 dated Jan. 10, 2017.
Geiselmann et al., "Fast optical modulation of the fluorescence from a single nitrogen-vacancy centre," Nature Physics 9: 785-789 (Dec. 2013; first published online Oct. 13, 2013), 5 pages.
Gombert & Blasi, "The Moth-Eye Effect-From Fundamentals to Commercial Exploitation," Functional Properties of Bio-Inspired Surfaces: 79-102, (Nov. 2009), 26 pages.
Gong et al., "Generation of Nitrogen-Vacancy Center Pairs in Bulk Diamond by Molecular Nitrogen Implantation," Chinese Physics Letters 33(2)(026105): 1-4 (Feb. 2016), 5 pages.
Gould et al., "An imaging magnetometer for bio-sensing based on nitrogen-vacancy centers in diamond," SPIE 8933, Frontiers in Biological Detection: From Nanosensors to Systems VI, 89330L (Mar. 18, 2014), 8 pages.
Gould et al., "Room-temperature detection of a single 19 nm superparamagnetic nanoparticle with an imaging magnetometer," Applied Physics Letters 105(072406): 1-4 (Aug. 19, 2014), 5 pages.
Gruber et al., "Scanning confocal optical microscopy and magnetic resonance on single defect centers," Science 276(5321): 2012-2014 (Jun. 27, 1997), 4 pages.
Haeberle et al., "Nanoscale nuclear magnetic imaging with chemical contrast," Nature Nanotechnology 10: 125-128 (Feb. 2015; first published online Jan. 5, 2015), 4 pages.
Haihua et al., "Design of wideband anti-reflective sub wavelength nanostructures," Infrared and Laser Engineering 40(2): 267-270 (Feb. 2011), 4 pages.
Hall et al., "Sensing of Fluctuating Nanoscale Magnetic Fields Using Nitrogen-Vacancy Centers in Diamond," Physical Review Letters 103(220802): 1-4 (Nov. 25, 2009), 4 pages.
Hanson et al., "Coherent Dynamics of a Single Spin Interacting with an Adjustable Spin Bath," Science 320(5874): 352-355 (Apr. 18, 2008), 5 pages.
Hanson et al., "Polarization and Readout of Coupled Single Spins in Diamond," Physical Review Letters 97(087601): 1-4 (Aug. 23, 2006), 4 pages.
Hanson et al., "Room-temperature manipulation and decoherence of a single spin in diamond," Physical Review 74(161203): 1-4 (Oct. 26, 2006), 4 pages.
Hanzawa et al., "Zeeman effect on the zero-phonon line of the NV center in synthetic diamond," Physica B 184(1-4): 137-140 (Feb. 1993), 4 pages.

(56) References Cited

OTHER PUBLICATIONS

Heerema, et al. "Graphene nanodevices for DNA sequencing." Nature nanotechnology 11.2 (Feb. 3, 2016): 127-136.
Hegyi & Yablonovitch, "Molecular imaging by optically detected electron spin resonance of nitrogen-vacancies in nanodiamonds," Nano Letters 13(3): 1173-1178 (Mar. 2013; first published online Feb. 6, 2013), 6 pages.
Hegyi & Yablonovitch, "Nanodiamond molecular imaging with enhanced contrast and expanded field of view," Journal of Biomedical Optics 19(1)(011015): 1-8 (Jan. 2014), 9 pages.
Hilser et al., "All-optical control of the spin state in the NV—center in diamond," Physical Review B 86(125204): 1-8 (Sep. 14, 2012), 8 pages.
Hobbs, "Study of the Environmental and Optical Durability of AR Microstructures in Sapphire, ALON, and Diamond," SPIE 7302, Window and Dome Technologies and Materials XI, 73020J (Apr. 27, 2009), 14 pages.
Huebener et al., "ODMR of NV centers in nano-diamonds covered with N@C60," Physica Status Solidi B 245(10): 2013-2017 (Oct. 2008; first published online Sep. 8, 2008), 5 pages.
Huxter et al., "Vibrational and electronic dynamics of nitrogen-vacancy centres in diamond revealed by two-dimensional ultrafast spectroscopy," Nature Physics 9: 744-749 (Sep. 29, 2013), 6 pages.
International Search Report and Written Opinion from related PCT application PCT/US2017/035315 dated Aug. 24, 2017, 7 pages.
International Search Report and Written Opinion of the International Searching Authority dated Apr. 1, 2016 from related PCT application PCT/US2016/014384, 12 pages.
International Search Report and Written Opinion of the International Searching Authority dated Apr. 11, 2016 from related PCT application PCT/US2016/014376, 12 pages.
International Search Report and Written Opinion of the International Searching Authority dated Apr. 11, 2016 from related PCT application PCT/US2016/014388, 14 pages.
International Search Report and Written Opinion of the International Searching Authority dated Apr. 11, 2016 from related PCT application PCT/US2016/014395, 15 pages.
International Search Report and Written Opinion of the International Searching Authority dated Apr. 4, 2017 from related PCT application PCT/US16/68366, 9 pages.
International Search Report and Written Opinion of the International Searching Authority dated Feb. 15, 2017 from related PCT application PCT/US2016/014390, 20 pages.
International Search Report and Written opinion of the International Searching Authority dated Jul. 12, 2016, from related PCT application PCT/US2016/014287, 14 pages.
International Search Report and Written Opinion of the International Searching Authority dated Jul. 16, 2015, from related PCT application PCT/US2015/24723, 8 pages.
International Search Report and Written Opinion of the International Searching Authority dated Jul. 6, 2015, from related PCT application PCT/US2015/021093, 9 pages.
International Search Report and Written Opinion of the International Searching Authority dated Jul. 8, 2015, from related PCT application PCT/US2015/024265, 11 pages.
International Search Report and Written Opinion of the International Searching Authority dated Jun. 1, 2017, from related PCT application PCT/US17/21811, 9 pages.
International Search Report and Written Opinion of the International Searching Authority dated Jun. 1, 2017, in related PCT application PCT/US17/22279, 20 pages.
International Search Report and Written Opinion of the International Searching Authority dated Jun. 2016 from related PCT application PCT/US2016/014290, 11 pages.
International Search Report and Written Opinion of the International Searching Authority dated Jun. 15, 2017, from related PCT application PCT/US2017/024175, 10 pages.
International Search Report and Written Opinion of the International Searching Authority dated Jun. 2, 2016, from related PCT application PCT/US2016/014386, 14 pages.
International Search Report and Written Opinion of the International Searching Authority dated Jun. 2, 2016, from related PCT application PCT/US2016/014387, 13 pages.
International Search Report and Written Opinion of the International Searching Authority dated Jun. 6, 2016, from related PCT application PCT/US2016/014291, 13 pages.
International Search Report and Written Opinion of the International Searching Authority dated Jun. 2016 from related PCT application PCT/US2016/014333, 16 pages.
International Search Report and Written Opinion of the International Searching Authority dated Jun. 9, 2017, from related patent application PCT/US2017/024181, 13 pages.
International Search Report and Written Opinion of the International Searching Authority dated Jun. 9, 2017, from related PCT application PCT/US2017/024179, 9 pages.
International Search Report and Written Opinion of the International Searching Authority dated Mar. 13, 2017 from related PCT application PCT/US2016/68320, 10 pages.
International Search Report and Written Opinion of the International Searching Authority dated Mar. 24, 2016 from related PCT application PCT/US2016/014336, 17 pages.
International Search Report and Written Opinion of the International Searching Authority dated Mar. 24, 2016 from related PCT application PCT/US2016/014297, 15 pages.
International Search Report and Written Opinion of the International Searching Authority dated Mar. 24, 2016 from related PCT application PCT/US2016/014392, 8 pages.
International Search Report and Written Opinion of the International Searching Authority dated Mar. 24, 2016 from related PCT application PCT/US2016/014403, 10 pages.
International Search Report and Written Opinion of the International Searching Authority dated Mar. 25, 2016, from related PCT application PCT/US2016/014363, 8 pages.
International Search Report and Written Opinion of the International Searching Authority dated Mar. 25, 2016, from related PCT application PCT/US2016/014389, 19 pages.
International Search Report and Written Opinion of the International Searching Authority dated Mar. 27, 2017 from related PCT application PCT/US16/68344, 16 pages.
International Search Report and Written Opinion of the International Searching Authority dated Mar. 28, 2016, from related PCT application PCT/US2016/014380, 9 pages.
International Search Report and Written Opinion of the International Searching Authority dated Mar. 28, 2016, from related PCT application PCT/US2016/014394, 17 pages.
International Search Report and Written Opinion of the International Searching Authority dated Mar. 29, 2016 from related PCT application PCT/US2016/014325, 11 pages.
International Search Report and Written Opinion of the International Searching Authority dated Mar. 29, 2016 from related PCT application PCT/US2016/014330, 8 pages.
International Search Report and Written Opinion of the International Searching Authority dated Mar. 29, 2016 from related PCT application PCT/US2016/014328, 7 pages.
International Search Report and Written Opinion of the International Searching Authority dated Mar. 29, 2016 from related PCT application PCT/US2016/014385, 11 pages.
International Search Report and Written Opinion of the International Searching Authority dated Mar. 30, 2016 from related PCT application PCT/US2016/014298, 14 pages.
International Search Report and Written Opinion of the International Searching Authority dated Mar. 31, 2016 from related PCT application PCT/US2016/014375, 11 pages.
International Search Report and Written Opinion of the International Searching Authority dated Mar. 31, 2016 from related PCT application PCT/US2016/014396, 11 pages.
International Search Report and Written Opinion of the International Searching Authority dated Mar. 31, 2017 from related PCT application PCT/US2016/066566, 11 pages.
International Search Report and Written Opinion of the International Searching Authority dated May 10, 2017 from related PCT application PCT/US17/19411, 8 pages.

(56) References Cited

OTHER PUBLICATIONS

International Search Report and Written Opinion of the International Searching Authority dated May 18, 2017, from related PCT application PCT/US2017/021593, 10 pages.
International Search Report and Written Opinion of the International Searching Authority dated May 19, 2017, from related PCT application PCT/US17/18099, 16 pages.
International Search Report and Written Opinion of the International Searching Authority dated May 26, 2016, from related PCT application PCT/US2016/014331, 15 pages.
International Search Report and Written Opinion of the International Searching Authority dated May 3, 2017 from related PCT application PCT/US2017/018701, 8 pages.
International Search Report and Written Opinion of the International Searching Authority dated May 4, 2017 from related PCT application PCT/US2017/018709, 8 pages.
International Search Report and Written Opinion of the International Searching Authority dated May 8, 2017 from related PCT application PCT/US2017/17321, 17 pages.
International Search Report and Written Opinion of the International Searching Authority dated Sep. 13, 2016, from related PCT application PCT/US16/14377, 11 pages.
International Search Report and Written Opinion of the International Searching Authority dated Jul. 14, 2017, from related PCT application PCT/US2017/022118, 13 pages.
International Search Report and Written Opinion of the International Searching Authority dated Jul. 17, 2017, from related PCT application PCT/US2017/024177, 11 pages.
International Search Report and Written Opinion of the International Searching Authority dated Jul. 18, 2017, from related PCT application PCT/US2017/024167, 11 pages.
International Search Report and Written Opinion of the International Searching Authority dated Jul. 18, 2017, from related PCT application PCT/US2017/024173, 13 pages.
International Search Report and Written Opinion of the International Searching Authority dated Jul. 19, 2017, from related PCT application PCT/US2017/024171, 12 pages.
International Search Report and Written Opinion of the International Searching Authority dated Jun. 15, 2017, from related PCT application PCT/US2017/024182, 21 pages.
International Search Report and Written Opinion of the International Searching Authority dated Jun. 22, 2017, in related PCT application PCT/US2017/024180, 10 pages.
International Search Report and Written Opinion of the International Searching Authority dated Jun. 5, 2017, from related PCT application PCT/US2017/024169, 11 pages.
International Search Report and Written Opinion of the International Searching Authority dated Jun. 5, 2017, from related PCT application PCT/US2017/024174, 8 pages.
International Search Report and Written Opinion of the International Searching Authority dated Jun. 5, 2017, in related PCT application PCT/US2017/024168, 7 pages.
International Search Report and Written Opinion of the International Searching Authority dated Jun. 6, 2017, from related PCT application PCT/2017/024165, 9 pages.
International Search Report and Written Opinion of the International Searching Authority dated Jun. 6, 2017, from related PCT application PCT/US2017/024172, 9 pages.
Ivady et al., "Pressure and temperature dependence of the zero-field splitting in the ground state of NV centers in diamond: A first-principles study," Physical Review B 90(235205): 1-8 (Dec. 2014), 8 pages.
Jarmola et al., "Temperature- and Magnetic-Field-Dependent Longitudinal Spin Relaxation in Nitrogen-Vacancy Ensembles in Diamond," Physical Review Letters 108 (197601): 1-5 (May 2012), 5 pages.
Jensen et al., "Light narrowing of magnetic resonances in ensembles of nitrogen-vacancy centers in diamond," Physical Review B 87(014115): 1-10 (Jan. 2013), 10 pages.
Kailath, "Linear Systems," Prentice Hall, (1979), 6 pages.

Karlsson et al., "Diamond micro-optics: microlenses and antireflection structures surfaces for the infrared spectral region," Optics Express 11(5): 502-507 (Mar. 10, 2003), 6 pages.
Keyser "Enhancing nanopore sensing with DNA nanotechnology." Nature nanotechnology 11.2 (Feb. 2016): 106-108.
Khan & Hemmer, "Noise limitation in nano-scale imaging," Proceedings of SPIE vol. 5842: 302-305, (Dec. 2005), 7 pages.
Kim et al., "Electron spin resonance shift and linewidth broadening of nitrogen-vacancy centers in diamond as a function of electron irradiation dose," Applied Physics Letters 101(082410): 1-5 (Aug. 2012), 6 pages.
Kim et al., "Jahn-Teller Splitting and Zeeman Effect of Acceptors in Diamond," Physica B 273-274: 647-627 (Jul. 1999), 4 pages.
Kim et al., "Magnetospectroscopy of acceptors in 'blue' diamonds," Physica B 302-301: 88-100 (Aug. 2001), 13 pages.
Kim et al., "Zeeman effect of electronic Raman lines of accepters in elemental semiconductors: Boron in blue diamond," Physical Review B 62(12): 8038-8052 (Sep. 2000), 15 pages.
King et al., "Optical polarization of 13C nuclei in diamond through nitrogen vacancy centers," Physical Review B 81(073201): 1-4 (Feb. 2010), 4 pages.
Kok et al., "Materials Science: Qubits in the pink," Nature 444(2): 49 (Nov. 2006), 1 page.
Konenko et al., "Formation of antireflective surface structures on diamond films by laser patterning," Applied Physics A 68:99-102 (Jan. 1999), 4 pages.
Kraus et al., "Magnetic field and temperature sensing with atomic-scale spin defects in silicon carbide," Scientific Reports 4(5303): 1-8 (Jul. 2014), 8 pages.
Lai et al., "Influence of a static magnetic field on the photoluminescence of an ensemble of nitrogen vacancy color centers in a diamond single-crystal," Applied Physics Letters 95, (Sep. 2009), 4 pages.
Lai et al., "Optically detected magnetic resonance of a single Nitrogen-Vacancy electronic spin in diamond nanocrystals," CLEO/EQEC, (Jun. 14-19, 2009), 1 page.
Laraoui et al., "Nitrogen-vacancy assisted magnetometry of paramagnetic centers in an individual diamond nanocrystal," Nano Letters 12: 3477-3482 (Jul. 2012), 6 pages.
Lazariev et al., "A nitrogen-vacancy spin based molecular structure microscope using multiplexed projection reconstruction," Scientific Reports 5(14130): 1-8 (Sep. 2015), 8 pages.
Le Sage et al., "Efficient photon detection from color centers in a diamond optical waveguide," Phys. Rev. B 85: 121202(R), pp. 121202-1-121202-4, (Mar. 23, 2012), 4 pages.
Lee et al., "Vector magnetometry based on S=3/2 electronic spins," Physical Review B 92 (115201): 1-7 (Sep. 2015), 7 pages.
Lesik et al., "Preferential orientation of NV defects in CVD diamond films grown on (113)-oriented substrates," Diamond and Related Materials 56: 47-53 (Jun. 2015), 7 pages.
Levchenko et al., "Inhomogeneous broadening of optically detected magnetic resonance of the ensembles of nitrogen-vacancy centers in diamond by interstitial carbon atoms," Applied Physics Letters 106, (Mar. 2015; published online Mar. 9, 2015), 6 pages.
Lindsay "The promises and challenges of solid-state sequencing." Nature nanotechnology 11.2 (Feb. 2016): 109-111.
Liu et al., "Electron spin studies of nitrogen vacancy centers in nanodiamonds," Acta Physica Sinica 62(16) 164208: 1-5 (Aug. 2013), 5 pages.
Liu et al., "Fiber-integrated diamond-based magnetometer," Applied Physics Letters 103(143105): 1-4 (Sep. 2013), 5 pages.
MacLaurin et al., "Nanoscale magnetometry through quantum control of nitrogen-vacancy centres in rotationally diffusing nanodiamonds," New Journal of Physics 15, (Jan. 2013), 16 pages.
MacQuarie et al., "Mechanical spin control of nitrogen-vacancy centers in diamond," Retrieved from http://www.arxiv.org/pdf/1306.6356.pdf, pp. 1-8, (Jun. 2013), 8 pages.
Macs et al., "Diamond as a magnetic field calibration probe," Journal of Physics D: Applied Physics 37, (Apr. 2004; published Mar. 17, 2004), 6 pages.
Maletinsky et al., "A robust scanning diamond sensor for nanoscale imaging with single nitrogen-vacancy centres," Nature Nanotechnology 7: 320-324, (May 2012; published Apr. 15, 2012), 5 pages.

(56) References Cited

OTHER PUBLICATIONS

Mamin et al., "Multipulse Double-Quantum Magnetometry with Near-Surface Nitrogen-Vacancy Centers," Physical Review Letters 13(030803): 1-5 (Jul. 2014), 5 pages.
Mamin et al., "Nanoscale Nuclear Magnetic Resonance with a Nitrogen-Vacancy Spin Sensor," Science 339, (Feb. 2013), 5 pages.
Manson et al., "GR transitions in diamond: magnetic field measurements," Journal of Physics C Solid St. Phys 13: L1005-L1009, (Nov. 1980), 6 pages.
Massachusetts Institute of Technology, "Wide-Field Imaging Using Nitrogen Vacancies," in Patent Application Approval Process, Physics Week: 1-5, (Jan. 20, 2015), 5 pages.
Matlashov, et al. "SQUIDs for magnetic resonance imaging at ultra-low magnetic field." PIERS online 5.5 (2009): 466-470.
Matlashov, et al. "SQUIDs vs. induction coils for ultra-low field nuclear magnetic resonance: experimental and simulation comparison." IEEE Transactions on Applied Superconductivity 21.3 (Jan. 1, 2012): 465-468.
Matsuda et al., "Development of a plastic diamond anvil cell for high pressure magneto-photoluminescence in pulsed high magnetic fields," International Journal of Modern Physics B 18(27-29), (Nov. 2004), 7 pages.
Maze et al., "Nanoscale magnetic sensing using spin qubits in diamond," Proc. SPIE 7225, Advanced Optical Concepts in Quantum Computing, Memory, and Communication II, 722509 (Feb. 2, 2009) 8 pages.
Maze et al., "Nanoscale magnetic sensing with an individual electronic spin in diamond," Nature Physics 455: 644-647 (Oct. 2, 2008), 5 pages.
Meijer et al., "Generation of single color centers by focused nitrogen implantation," Applied Physics Letters 87(261909): 1-3 (Dec. 2005), 4 pages.
Michaelovich et al., "Polarization Dependencies of the Nitrogen-Vacancy Center." Undergraduate Project Report, Ben-Gurion University, Aug. 2015, pp. 1-9.
Millot et al., "High-field Zeeman and Paschen-Back effects at high pressure in oriented ruby," Physical Review B 78 (155125): 1-7 (Oct. 2008), 7 pages.
Moessle, et al. "SQUID-detected magnetic resonance imaging in microtesla fields." Annu. Rev. Biomed. Eng. 9 (May 23, 2008): 389-413.
Moriyama et al., "Importance of electron-electron interactions and Zeeman splitting in single-wall carbon nanotube quantum dots," Physica E 26: 473-476 (Feb. 2005), 4 pages.
Mrozek et al., "Circularly polarized microwaves for magnetic resonance study in the GHz range: Application to nitrogen-vacancy in diamonds," Applied Physics Letters, pp. 1-4 (Jul. 2015), 4 pages.
Nagl et al., "Improving surface and defect center chemistry of fluorescent nanodiamonds for imaging purposes—a review," Analytical and Bioanalaytical Chemistry 407: 7521-7536 (Oct. 2015; published online Jul. 29, 2015), 16 pages.
Neumann et al., "Excited-state spectroscopy of single NV defects in diamond using optically detected magnetic resonance," New Journal of Physics 11(013017): 1-10, (Jan. 2009), 11 pages.
Nizovtsev & Kilin, "Optically Detected Magnetic Resonance Spectra of the 14NV-13C Spin Systems in Diamond: Analytical Theory and Experiment," Doklady of the National Academy of Sciences of Belarus, (2013), 27 pages with English machine translation.
Nizovtsev et al., "Modeling fluorescence of single nitrogen-vacancy defect centers in diamond," Physica B—Condensed Matter, 608-611 (Dec. 2001), 4 pages.
Nizovtsev et al., "Theoretical study of hyperfine interactions and optically detected magnetic resonance spectra by simulation of the C-291(NV)H-(172) diamond cluster hosting nitrogen-vacancy center," New Journal of Physics 16(083014): 1-21 (Aug. 2014), 22 pages.
Nobauer et al., "Smooth optimal quantum control for robust solid state spin magnetometry," Retrieved from http://www.arxiv.org/abs/1412.5051, pp. 1-12, (Dec. 2014), 12 pages.
Nowodzinski et al., "Nitrogen-Vacancy centers in diamond for current imaging at the redistributive layer level of Integrated Circuits," Microelectronics Reliability 55: 1549-1553 (Aug. 2015), 5 pages.
Nusran et al., "Optimizing phase-estimation algorithms for diamond spin magnetometry," Physical Review B 90(024422): 1-12 (Jul. 2014), 12 pages.
Ohashi et al., "Negatively Charged Nitrogen-Vacancy Centers in a 5 nm Thin 12C Diamond Film," Nano Letters 13: 4733-4738 (Oct. 2013), 6 pages.
Pelliccione, et al., Two-dimensional nanoscale imaging of gadolinium spins via scanning probe relaxometry with a single spin in diamond, Phys. Rev. Applied 2.5, (Sep. 8, 2014): 054014 pp. 1-17.
Plakhotnik et al., "Super-Paramagnetic Particles Chemically Bound to Luminescent Diamond : Single Nanocrystals Probed with Optically Detected Magnetic Resonance," Journal of Physical Chemistry C 119: 20119-20124 (Aug. 2015), 6 pages.
Polatomic. "AN/ASQ-233A Digital Magnetic Anomaly Detective Set." Retrieved May 9, 2016, from http://polatomic.com/images/DMAD_Data_Sheet_09-2009.pdf (2009), 1 page.
Poole, "What is GMSK Modulation—Gaussian Minimum Shift Keying." Radio-Electronics, retrieved from https://web.archive.org/web/20150403045840/http://www.radio-electronics.com/info/rf-technology-design/pm-phase-modulation/what-is-gmsk-gaussian-minimum-shift-keyingtutorial.php (Apr. 3, 2015), 4 pages.
Qiu et al., "Low-field NMR Measurement Procedure when SQUID Detection is Used," IEEE/CSC & ESAS European Superconductivity News Forum, No. 5, Jul. 2008.
Qiu, et al. "SQUID-detected NMR in Earth's magnetic field." Journal of Physics: Conference Series. vol. 97. No. 1. IOP Publishing, Mar. 2008, pp. 1-7.
Rabeau et al., "Implantation of labelled single nitrogen vacancy centers in diamond using 15N," Applied Physics Letters 88, (Jan. 2006), 4 pages.
Ramsey, et al., "Phase Shifts in the Molecular Beam Method of Separated Oscillating Fields", Physical Review, vol. 84, No. 3, Nov. 1, 1951, pp. 506-507.
Ranjbar et al., "Many-electron states of nitrogen-vacancy centers in diamond and spin density calculations," Physical Review B 84(165212): 1-6 (Oct. 2011), 6 pages.
Reynhardt, "Spin-lattice relaxation of spin-1/2 nuclei in solids containing diluted paramagnetic impurity centers. I. Zeeman polarization of nuclear spin system," Concepts in Magnetic Resonance Part A, pp. 20-35, (Sep. 2003), 16 pages.
Rogers et al., "Singlet levels of the NV(-) centre in diamond," New Journal of Physics 17, (Jan. 2015), 13 pages.
Rondin et al., "Magnetometry with nitrogen-vacancy defects in diamond," Reports on Progress in Physics 77(056503) 1-26 (May 2014), 27 pages.
Rondin et al., "Magnetometry with nitrogen-vacancy defects in diamond." May 22, 2014 (May 22, 2014), pp. 1 [online] http://arxiv.org/pdf/1311.5214.pdf, 29 pages.
Rondin et al., "Nanoscale magnetic field mapping with a single spin scanning probe magnetometer," Applied Physics Letters 100, (Apr. 2012), 5 pages.
Sarkar et al., "Magnetic properties of graphite oxide and reduced graphene oxide," Physica E 64: 78-82 (Nov. 2014), 5 pages.
Scheuer et al., "Accelerated 2D magnetic resonance spectroscopy of single spins using matrix completion," Scientific Reports 5(17728): 1-8 (Dec. 2015), 8 pages.
Schirhagl et al., "Nitrogen-vacancy centers in diamond: Nanoscale sensors for physics and biology," Annual Review of Physical Chemistry 65: 83-105 (Jan. 2014), 26 pages.
Schoenfeld & Harneit, "Real time magnetic field sensing and imaging using a single spin in diamond," Physical Review Letters 106(030802): 1-4 (Jan. 2011), 4 pages.
Sedov et al., "Si-doped nano- and microcrystalline diamond films with controlled bright photoluminescence of silicon-vacancy color centers," Diamond and Related Materials 56: 23-28 (Jun. 2015; available online Apr. 18, 2015), 6 pages.
Shames et al., "Magnetic resonance tracking of fluorescent nanodiamond fabrication," Journal of Physics D: Applied Physics 48(155302): 1-13 (Apr. 2015; published Mar. 20, 2015), 14 pages.

(56) References Cited

OTHER PUBLICATIONS

Shao et al., "Diamond Color Center Based FM Microwave Demodulator," in Conference on Lasers and Electro-Optics, OSA Technical Digest (online) (Optical Society of America), paper JTh2A.136, (Jun. 5-10, 2016), 2 pages.
Sheinker et al., "Localization in 3-D Using Beacons of Low Frequency Magnetic Field." IEEE Transactions on Instrumentation and Measurement 62(12): 3194-3201 (Dec. 2013), 8 pages.
Simanovskaia et al., "Sidebands in optically detected magnetic resonance signals of nitrogen vacancy centers in diamond," Physical Review B 87(224106): 1-11 (Jun. 2013), 11 pages.
Sotoma et al., "Effective production of fluorescent nanodiamonds containing negatively-charged nitrogen-vacancy centers by ion irradiation," Diamond and Related Materials 49: 33-38 (Oct. 2014), 6 pages.
Soykal et al., "Quantum metrology with a single spin-3/2 defect in silicon carbide," Mesoscale and Nanoscale Physics (May 24, 2016), retrieved from https://arxiv.org/abs/1605.07628 (Sep. 22, 2016), 9 pages.
Steiner et al., "Universal enhancement of the optical readout fidelity of single electron spins at nitrogen-vacancy centers in diamond," Physical Review B 81(035205): 1-6 (Jan. 2010), 6 pages.
Steinert et al., "High-sensitivity magnetic imaging using an array of spins in diamond," Rev. Sci. Inst. 81(043705): 1-5 (Apr. 23, 2010), 5 pages.
Steinert et al., "Magnetic spin imaging under ambient conditions with sub-cellular resolution." Nature Comms 4:1607 (Mar. 19, 2013).
Stepanov et al., "High-frequency and high-field optically detected magnetic resonance of nitrogen-vacancy centers in diamond," Applied Physics Letters 106, (Feb. 2015), 5 pages.
Sternschulte et al., "Uniaxial stress and Zeeman splitting of the 1.681 eV optical center in a homoepitaxial CVD diamond film," Diamond and Related Materials 4: 1189-1192 (Sep. 1995), 4 pages.
Storteboom et al., "Lifetime investigation of single nitrogen vacancy centres in nanodiamonds," Optics Express 23(9): 11327-11333 (May 4, 2015; published Apr. 22, 2015), 7 pages.
Sushkov, et al. "All-optical sensing of a single-molecule electron spin." Nano letters 14.11 (Nov. 7, 2013): 6443-6448.
Tahara et al., "Quantifying selective alignment of ensemble nitrogen-vacancy centers in (111) diamond," Applied Physics Letters 107:193110 (Nov. 2015; published online Nov. 13, 2015), 5 pages.
Taylor et al., "High-sensitivity diamond magnetometer with nanoscale resolution," Nature Physics 4: 810-816 (Oct. 2008), 7 pages.
Teale, "Magnetometry with Ensembles of Nitrogen Vacancy Centers in Bulk Diamond," Master's Thesis, Massachusetts Institute of Technology Department of Electrical Engineering and Computer Science (Sep. 2015), 57 pages.
Terblanche et al., "13C spin-lattice relaxation in natural diamond: Zeeman relaxation at 4.7 T and 300 K due to fixed paramagnetic nitrogen defects," Solid State Nuclear Magnetic Resonance 20: 1-22 (Aug. 2001), 22 pages.
Terblanche et al., "13C spin-lattice relaxation in natural diamond: Zeeman relaxation in fields of 500 to 5000 G at 300 K due to fixed paramagnetic nitrogen defects," Solid State Nuclear Magnetic Resonance 19: 107-129 (May 2001), 23 pages.
Tetienne et al., "Magnetic-field-dependent photodynamics of single NV defects in diamond: an application to qualitative all-optical magnetic imaging," New Journal of Physics 14(103033): 1-5 (Oct. 2012), 16 pages.
Tetienne, et al. "Spin relaxometry of single nitrogen-vacancy defects in diamond nanocrystals for magnetic noise sensing." Physical Review B 87.23 (Apr. 3, 2013): 235436-1-235436-5.
Tong et al., "A hybrid-system approach for W state and cluster state generation," Optics Communication 310: 166-172, (Jan. 2014; available online Aug. 12, 2013), 7 pages.
Uhlen et al., "New diamond nanofabrication process for hard x-ray zone plates," J. of Vacuum Science & Tech. B 29(6) (06FG03): 1-4 (Nov./Dec. 2011), 4 pages.

U.S. Corrected Notice of Allowance dated Jun. 29, 2017 from related U.S. Appl. No. 15/351,862, 4 pages.
U.S. Notice of Allowance dated Apr. 20, 2016, from related U.S. Appl. No. 15/003,718, 9 pages.
U.S. Notice of Allowance dated Aug. 11, 2017 from related U.S. Appl. No. 15/003,558, 5 pages.
U.S. Notice of Allowance dated Aug. 17, 2016, from related U.S. Appl. No. 15/003,718, 8 pages.
U.S. Notice of Allowance dated Dec. 13, 2016, from related U.S. Appl. No. 14/680,877, 8 pages.
U.S. Notice of Allowance dated Dec. 22, 2016, from related U.S. Appl. No. 14/659,498, 10 pages.
U.S. Notice of Allowance dated Feb. 14, 2017, from related U.S. Appl. No. 15/003,677, 8 pages.
U.S. Notice of Allowance dated Jul. 18, 2017 from related U.S. Appl. No. 15/003,634, 6 pages.
U.S. Notice of Allowance dated Jul. 24, 2017 from related U.S. Appl. No. 15/003,088, 12 pages.
U.S. Notice of Allowance dated Jun. 20, 2017, from related U.S. Appl. No. 15/204,675, 9 pages.
U.S. Notice of Allowance dated Jun. 28, 2017 from related U.S. Appl. No. 15/003,256, 10 pages.
U.S. Notice of Allowance dated Jun. 8, 2017, from related U.S. Appl. No. 15/351,862, 7 pages.
U.S. Notice of Allowance dated Mar. 15, 2017, from related U.S. Appl. No. 15/351,862, 6 pages.
U.S. Notice of Allowance dated Mar. 29, 2016, from related U.S. Appl. No. 15/003,590, 11 pages.
U.S. Notice of Allowance dated May 26, 2017 from related U.S. Appl. No. 15/218,821, 7 pages.
U.S. Notice of Allowance dated Sep. 1, 2017, from related U.S. Appl. No. 14/676,740, 7 pages.
U.S. Notice of Allowance dated Sep. 14, 2017, from related U.S. Appl. No. 15/476,636, 10 pages.
U.S. Notice of Allowance dated Sep. 18, 2017, from related U.S. Appl. No. 15/003,206, 11 pages.
U.S. Notice of Allowance dated Sep. 26, 2017 from related U.S. Appl. No. 15/003,281, 7 pages.
U.S. Notice of Allowance dated Sep. 8, 2016, from related U.S. Appl. No. 15/003,298, 10 pages.
U.S. Office Action dated Apr. 17, 2017, from related U.S. Appl. No. 15/003,558, 12 pages.
U.S. Office Action dated Aug. 15, 2017 from related U.S. Appl. No. 15/003,281, 12 pages.
U.S. Office Action dated Aug. 24, 2016 from related U.S. Appl. No. 14/676,740, 19 pages.
U.S. Office Action dated Feb. 10, 2017, from related U.S. Appl. No. 15/003,088, 11 pages.
U.S. Office Action dated Feb. 16, 2017, from related U.S. Appl. No. 15/204,675, 7 pages.
U.S. Office Action dated Jul. 27, 2017 from related U.S. Appl. No. 15/003,577, 15 pages.
U.S. Office Action dated Jul. 29, 2016 from related U.S. Appl. No. 14/680,877, 8 pages.
U.S. Office Action dated Jun. 1, 2017, from related U.S. Appl. No. 15/003,797, 29 pages.
U.S. Office Action dated Jun. 1, 2017, from related U.S. Appl. No. 15/179,957, 29 pages.
U.S. Office Action dated Jun. 12, 2017, from related U.S. Appl. No. 15/003,256, 9 pages.
U.S. Office Action dated Jun. 12, 2017, from related U.S. Appl. No. 15/003,336, 14 pages.
U.S. Office Action dated Jun. 16, 2017, from related U.S. Appl. No. 15/003,678, 15 pages.
U.S. Office Action dated Jun. 2, 2017, from related U.S. Appl. No. 15/476,636, 10 pages.
U.S. Office Action dated Mar. 1, 2017, from related U.S. Appl. No. 15/003,634, 7 pages.
U.S. Office Action dated Mar. 16, 2017, from related U.S. Appl. No. 15/218,821, 7 pages.
U.S. Office Action dated May 13, 2016, from related U.S. Appl. No. 14/676,740, 15 pages.

(56) References Cited

OTHER PUBLICATIONS

U.S. Office Action dated May 22, 2017, from related U.S. Appl. No. 15/003,206, 12 pages.
U.S. Office Action dated May 6, 2016, from related U.S. Appl. No. 14/659,498.
U.S. Office Action dated Nov. 2, 2016, from related U.S. Appl. No. 15/003,256, 19 pages.
U.S. Office Action dated Nov. 3, 2016, from related U.S. Appl. No. 15/204,675, 9 pages.
U.S. Office Action dated Oct. 14, 2016 from related U.S. Appl. No. 15/003,677, 13 pages.
U.S. Office Action dated Oct. 19, 2016, from related U.S. Appl. No. 15/218,821, 6 pages.
U.S. Office Action dated Sep. 27, 2017, from related U.S. Appl. No. 15/003,176, 8 pages.
U.S. Office Action dated Sep. 8, 2017, from related U.S. Appl. No. 15/003,292, 8 pages.
Vershovskii & Dmitriev, "Combined excitation of an optically detected magnetic resonance in nitrogen-vacancy centers in diamond for precision measurement of the components of a magnetic field vector," Technical Physics Letters 41(11): 1026-1029 (Nov. 2015), 4 pages.
Vershovskii & Dmitriev, "Micro-scale three-component quantum magnetometer based on nitrogen-vacancy color centers in diamond crystal," Technical Physics Letters 41(4): 393-396 (Apr. 2015), 4 pages.
Wahlstrom et al., "Modeling Magnetic Fields Using Gaussian Processes," 2013 IEEE International Conference on Acoustics, Speech, and Signal Processing, pp. 3522-3526 (May 26-31, 2013), 5 pages.
Wang et al., "Optimizing ultrasensitive single electron magnetometer based on nitrogen-vacancy center in diamond," Chinese Science Bulletin, 58(24): 2920-2923, (Aug. 2013), 4 pages.
Webber et al., "Ab initio thermodynamics calculation of the relative concentration of NV- and NV0 defects in diamond," Physical Review B 85,(014102): 1-7 (Jan. 2012), 7 pages.
Wells, et al. "Assessing graphene nanopores for sequencing DNA." Nano letters 12.8 (Jul. 10, 2012): 4117-4123.
Widmann et al., "Coherent control of single spins in silicon carbide at room temperature," Nature Materials, 14: 164-168 (2015) (available online Dec. 1, 2014), 5 pages.
Wolf et al., "Subpicotesla Diamond Magnetometry," Physical Review X 5(041001): 1-10 (Oct. 2015), 10 pages.
Wolfe et al., "Off-resonant manipulation of spins in diamond via precessing magnetization of a proximal ferromagnet," Physical Review B 89(180406): 1-5 (May 2014), 5 pages.
Wroble, "Performance Analysis of Magnetic Indoor Local Positioning System." Western Michigan University Master's Theses, Paper 609 (Jun. 2015), 42 pages.
Wysocki et al., "Modified Walsh-Hadamard sequences for DS CDMA wireless systems." Int. J. Adaptive Control and Signal Processing 16(8): 589-602 (Oct. 2002; first published online Sep. 23, 2002), 25 pages.
Xue & Liu, "Producing GHZ state of nitrogen-vacancy centers in cavity QED," Journal of Modern Optics 60(6-7), (Mar. 2013), 8 pages.
Yang & Gu, "Novel calibration techniques for high pulsed-magnetic fields using luminescence caused by photo," (with English machine translation), Journal of Huazhong University of Science and Technology, (Jun. 2007), 11 pages.
Yavkin et al., "Defects in Nanodiamonds: Application of High-Frequency cw and Pulse EPR, ODMR," Applied Magnetic Resonance, 45: 1035-1049 (Oct. 2014; published online Sep. 10, 2014), 15 pages.
Yu et al., "Bright fluorescent nanodiamonds: no photobleaching and low cytotoxicity," J. Am. Chem. Soc., 127: 17604-17605 (Nov. 25, 2005), 2 pages.
Zhang et al., "Laser-polarization-dependent and magnetically controlled optical bistability in diamond nitrogen-vacancy centers," Physics Letters A 377: 2621-2627 (Nov. 2013), 7 pages.
Zhang et al., "Laser-polarization-dependent spontaneous emission of the zero phonon line from single nitrogen-vacancy center in diamond," Chinese Physics B 24(3), (Apr. 2014), 13 pages.
Zhang et al., "Scalable quantum information transfer between nitrogen-vacancy-center ensembles," Annals of Physics, 355: 170-181 (Apr. 2015; available online Feb. 14, 2013), 12 pages.
Zhao et al., "Atomic-scale magnetometry of distant nuclear spin clusters via nitrogen-vacancy spin in diamond," Nature Nanotechnology, 5: 242-246 (Apr. 2011), 5 pages.
U.S. Appl. No. 14/659,498, filed Mar. 16, 2015, U.S. Pat. No. 9,638,821.
PCT/US2015/021093, Mar. 17, 2015, WO2015142945.
U.S. Appl. No. 14/676,740, filed Apr. 1, 2015, 20150326410.
PCT/US2015/024265, Apr. 3, 2015, WO2015157110.
PCT/US2015/024723, Apr. 7, 2015, WO2015157290.
U.S. Appl. No. 14/680,877, filed Apr. 7, 2015, U.S. Pat. No. 9,590,601.
U.S. Appl. No. 14/866,730, filed Sep. 25, 2015, 20160146904.
U.S. Appl. No. 15/003,678, filed Jan. 21, 2016, 20170212183.
U.S. Appl. No. 15/003,281, filed Jan. 21, 2016, 20170212178.
U.S. Appl. No. 15/003,292, filed Jan. 21, 2016, 20170212179.
U.S. Appl. No. 15/003,298, filed Jan. 21, 2016, U.S. Pat. No. 9,551,763.
U.S. Appl. No. 15/003,309, filed Jan. 21, 2016, 20170212180.
U.S. Appl. No. 15/003,176, filed Jan. 21, 2016, 20170123015.
U.S. Appl. No. 15/003,145, filed Jan. 21, 2016, 20170199156.
U.S. Appl. No. 15/003,336, filed Jan. 21, 2016, 20170212181.
U.S. Appl. No. 15/003,558, filed Jan. 21, 2016, 20170146617.
U.S. Appl. No. 15/003,519, filed Jan. 21, 2016, 20170146616.
U.S. Appl. No. 15/003,677, filed Jan. 21, 2016, U.S. Pat. No. 9,614,589.
U.S. Appl. No. 15/003,256, Jan. 21, 2016, 20170212177.
U.S. Appl. No. 15/003,577, filed Jan. 21, 2016, 20170212046.
U.S. Appl. No. 15/003,704, filed Jan. 21, 2016, 20160231394.
U.S. Appl. No. 15/003,718, filed Jan. 21, 2016, U.S. Pat. No. 9,541,610.
U.S. Appl. No. 15/003,062, filed Jan. 21, 2016, 20170023487.
U.S. Appl. No. 15/003,652, filed Jan. 21, 2016, 20170010594.
U.S. Appl. No. 15/003,634, filed Jan. 21, 2016, 20170212182.
U.S. Appl. No. 15/003,670, filed Jan. 21, 2016, 20170212190.
U.S. Appl. No. 15/003,088, filed Jan. 21, 2016, 20160214714.
U.S. Appl. No. 15/003,797, filed Jan. 21, 2016, 20160216341.
U.S. Appl. No. 15/003,590, filed Jan. 21, 2016, U.S. Pat. No. 9,557,391.
U.S. Appl. No. 15/003,206, filed Jan. 21, 2016, 20170110015.
U.S. Appl. No. 15/003,193, filed Jan. 21, 2016, 20160216304.
U.S. Appl. No. 15/003,617, filed Jan. 21, 2016, 20170010334.
U.S. Appl. No. 15/003,396, filed Jan. 21, 2016, 20170068012.
U.S. Appl. No. 15/003,177, filed Jan. 21, 2016, 20170212258.
U.S. Appl. No. 15/003,209, filed Jan. 21, 2016, 20170211947.
PCT/US2016/014389, Jan. 21, 2016, WO2017078766.
PCT/US2016/014336, Jan. 21, 2016, WO2016118756.
PCT/US2016/014403, Jan. 21, 2016, WO2016118791.
PCT/US2016/014331, Jan. 21, 2016, WO2016126435.
PCT/US2016/014387, Jan. 21, 2016, WO2017014807.
PCT/US2016/014390, Jan. 21, 2016, WO2016190909.
PCT/US2016/014385, Jan. 21, 2016, WO2016122966.
PCT/US2016/014375, Jan. 21, 2016, WO2016122965.
PCT/US2016/014298, Jan. 21, 2016, WO2017007514.
PCT/US2016/014297, Jan. 21, 2016, WO2017007513.
PCT/US2016/014377, Jan. 21, 2016, WO2017039747.
PCT/US2016/014392, Jan. 21, 2016, WO2017127095.
PCT/US2016/014395, Jan. 21, 2016, WO2017127097.
PCT/US2016/014394, Jan. 21, 2016, WO2017127096.
PCT/US2016/014386, Jan. 21, 2016, WO2017127094.
PCT/US2016/014333, Jan. 21, 2016, WO2016126436.
PCT/US2016/014328, Jan. 21, 2016, WO2017087014.
PCT/US2016/014325, Jan. 21, 2016, WO2017087013.
PCT/US2016/014330, Jan. 21, 2016, WO2017127085.
PCT/US2016/014388, Jan. 21, 2016, WO2017095454.
PCT/US2016/014380, Jan. 21, 2016, WO2017123261.
PCT/US2016/014290, Jan. 21, 2016, WO2017127080.
PCT/US2016/014363, Jan. 21, 2016, WO2017127090.

(56) References Cited

OTHER PUBLICATIONS

PCT/US2016/014287, Jan. 21, 2016, WO2017127079.
PCT/US2016/014291, Jan. 21, 2016, WO2017127081.
PCT/US2016/014396, Jan. 21, 2016, WO2017127098.
PCT/US2016/014384, Jan. 21, 2016, WO2017127093.
PCT/US2016/014376, Jan. 21, 2016, WO2017127091.
U.S. Appl. No. 15/179,957, filed Jun. 10, 2016, 20160356863.
U.S. Appl. No. 15/207,457, filed Jul. 11, 2016.
U.S. Appl. No. 15/218,821, filed Jul. 25, 2016, 20170212185.
U.S. Appl. No. 15/204,675, filed Jul. 7, 2016, 20170212184.
U.S. Appl. No. 15/350,303, filed Nov. 14, 2016.
U.S. Appl. No. 15/351,862, filed Nov. 15, 2016, U.S. Pat. No. 9,720,055.
U.S. Appl. No. 15/372,201, filed Dec. 7, 2016, 20170212187.
U.S. Appl. No. 15/376,244, filed Dec. 12, 2016.
PCT/US2016/066566, Dec. 14, 2016.
U.S. Appl. No. 15/380,691, filed Dec. 15, 2016.
U.S. Appl. No. 15/382,045, filed Dec. 16, 2016.
U.S. Appl. No. 15/380,419, filed Dec. 15, 2016.
PCT/US2016/068320, Dec. 22, 2016.
PCT/US2016/068344, Dec. 22, 2016.
PCT/US2016/068366, Dec. 22, 2016.
U.S. Appl. No. 15/419,832, filed Jan. 30, 2017, 20170139017.
U.S. Appl. No. 15/400,794, filed Jan. 6, 2017, 20170115361.
U.S. Appl. No. 15/443,422, filed Feb. 27, 2017.
PCT/US2017/017321, Feb. 10, 2017.
PCT/US2017/018099, Feb. 16, 2017.
U.S. Appl. No. 15/437,222, filed Feb. 20, 2017, 20170120293.
U.S. Appl. No. 15/437,038, filed Feb. 20, 2017.
PCT/US2017/018709, Feb. 21, 2017.
PCT/US2017/018701, Feb. 21, 2017.
U.S. Appl. No. 15/440,194, filed Feb. 23, 2017.
PCT/US2017/019411, Feb. 24, 2017.
U.S. Appl. No. 15/446,373, filed Mar. 1, 2017.
U.S. Appl. No. 15/450,504, filed Mar. 6, 2017.
U.S. Appl. No. 15/454,162, filed Mar. 9, 2017.
PCT/US2017/021593, Mar. 9, 2017.
PCT/US2017/021811, Mar. 10, 2017.
U.S. Appl. No. 15/456,913, filed Mar. 13, 2017.
PCT/US2017/022118, Mar. 13, 2017.
PCT/US2017/022279, Mar. 14, 2017.
U.S. Appl. No. 15/468,356, filed Mar. 24, 2017.
U.S. Appl. No. 15/468,397, filed Mar. 24, 2017.
U.S. Appl. No. 15/468,386, filed Mar. 24, 2017.
U.S. Appl. No. 15/468,289, filed Mar. 24, 2017.
U.S. Appl. No. 15/468,641, filed Mar. 24, 2017.
U.S. Appl. No. 15/468,582, filed Mar. 24, 2017.
U.S. Appl. No. 15/468,410, filed Mar. 24, 2017.
U.S. Appl. No. 15/468,951, filed Mar. 24, 2017.
U.S. Appl. No. 15/468,559, filed Mar. 24, 2017.
U.S. Appl. No. 15/468,282, filed Mar. 24, 2017.
U.S. Appl. No. 15/468,314, filed Mar. 24, 2017.
U.S. Appl. No. 15/468,274, filed Mar. 24, 2017.
U.S. Appl. No. 15/468,303, filed Mar. 24, 2017.
U.S. Appl. No. 15/469,374, filed Mar. 24, 2017.
PCT/US2017/024165, Mar. 24, 2017.
PCT/US2017/024167, Mar. 24, 2017.
PCT/US2017/024168, Mar. 24, 2017.
PCT/US2017/024169, Mar. 24, 2017.
PCT/US2017/024171, Mar. 24, 2017.
PCT/US2017/024172, Mar. 24, 2017.
PCT/US2017/024173, Mar. 24, 2017.
PCT/US2017/024174, Mar. 24, 2017.
PCT/US2017/024175, Mar. 24, 2017.
PCT/US2017/024177, Mar. 24, 2017.
PCT/US2017/024179, Mar. 24, 2017.
PCT/US2017/024180, Mar. 24, 2017.
PCT/US2017/024181, Mar. 24, 2017.
PCT/US2017/024182, Mar. 24, 2017.
U.S. Appl. No. 15/476,636, filed Mar. 31, 2017, 20170205526.
U.S. Appl. No. 15/479,256, filed Apr. 4, 2017, 20170207823.
U.S. Appl. No. 15/610,526, filed May 31, 2017.
PCT/US2017/035315, May 31, 2017.
U.S. Appl. No. 15/672,953, filed Aug. 9, 2017.
Teeling-Smith et al., "Electron Paramagnetic Resonance of a Single NV Nanodiamond Attached to an Individual Biomolecule", Biophysical Journal 110, May 10, 2016, pp. 2044-2052.
UK Office Action dated Jun. 8, 2018, from related application No. GB1617438.5, 3 pages.
U.S. Final Office Action dated Jul. 26, 2018 from related U.S. Appl. No. 15/003,177, 14 pages.
U.S. Non-Final Office Action dated Aug. 6, 2018 from related U.S. Appl. No. 15/376,244, 28 pages.
U.S. Non-Final Office Action dated Aug. 9, 2018 from related U.S. Appl. No. 15/003,309, 22 pages.
U.S. Non-Final Office Action dated Jul. 20, 2018 from related U.S. Appl. No. 15/350,303, 13 pages.
U.S. Non-Final Office Action dated Jul. 26, 2018 from related U.S. Appl. No. 15/380,419, 11 pages.
U.S. Non-Final Office Action dated Jul. 3, 2018 from related U.S. Appl. No. 15/003,396, 19 pages.
U.S. Notice of Allowance dated Jul. 18, 2018 from related U.S. Appl. No. 15/468,386, 12 pages.
U.S. Notice of Allowance dated Jul. 6, 2018 from related U.S. Appl. No. 15/672,953, 11 pages.
U.S. Notice of Allowance dated Jun. 27, 2018 from related U.S. Appl. No. 15/003,519, 21 pages.
U.S. Notice of Allowance dated May 15, 2018, from related U.S. Appl. No. 15/003,209, 7 pages.
U.S. Notice of Allowance dated May 16, 2018 from related U.S. Appl. No. 15/003,145, 8 pages.
U.S. Office Action dated Jun. 19, 2018, from related U.S. Appl. No. 15/450,504, 12 pages.
European Extended Search Report for Appl. Ser. No. 16740794.9 dated Nov. 12, 2018, 12 pages.
Halbach et al., "Design of Permanent Multipole Magnets with Oriented Rare Earth Cobalt Material", Nuclear Instruments and Methods, North Holland Publishing Co., Amsterdam, NL., vol. 169, Jan. 1, 1980, pp. 1-5, XP001032085, DOI: 10.1016/0029-554X(80)90094-4.
Hodges et al., "Time-keeping with electron spin states in diamond", Dept. of Electrical Engineering and Dept. of Applied Physics and Applied Mathematics, Columbia University, New York, New York 10027, Aug. 30, 2011, 13 pages.
Hodges et al., Appendix, "Time-keeping with electron spin states in diamond", Dept. of Electrical Engineering and Dept. of Applied Physics and Applied Mathematics, Columbia University, New York, New York 10027, Aug. 27, 2012, 46 pages.
International Search Report and Written Opinion for PCT Appl. Ser. No. PCT/US2018/041527 dated Feb. 4, 2019, 22 pages.
U.S. Ex Parte Quayle Action for U.S. Appl. No. 15/468,641 dated Nov. 28, 2018, 11 pages.
U.S. Non-Final Office Action for U.S. Appl. No. 15/003,177 dated Jan. 14, 2019, 15 pages.
U.S. Non-Final Office Action for U.S. Appl. No. 15/003,670 dated Nov. 27, 2018, 14 pages.
U.S. Non-Final Office Action for U.S. Appl. No. 15/382,045 dated Dec. 31, 2018, 16 pages.
U.S. Non-Final Office Action for U.S. Appl. No. 15/400,794 dated Jan. 10, 2019, 6 pages.
U.S. Non-Final Office Action for U.S. Appl. No. 15/468,356 dated Jan. 2, 2019, 10 pages.
U.S. Non-Final Office Action for U.S. Appl. No. 15/468,951 dated Dec. 13, 2018, 9 pages.
U.S. Notice of Allowance for U.S. Appl. No. 15/003,670 dated Feb. 1, 2019, 7 pages.
U.S. Notice of Allowance for U.S. Appl. No. 15/350,303 dated Dec. 26, 2018, 10 pages.
U.S. Notice of Allowance for U.S. Appl. No. 15/450,504 dated Dec. 13, 2018, 7 pages.
U.S. Notice of Allowance for U.S. Appl. No. 15/454,162 dated Jan. 17, 2019, 8 pages.

(56) References Cited

OTHER PUBLICATIONS

U.S. Notice of Allowance for U.S. Appl. No. 15/468,397 dated Dec. 12, 2018, 5 pages.
U.S. Notice of Allowance for U.S. Appl. No. 15/468,641 dated Feb. 7, 2019, 10 pages.
U.S. Notice of Allowance for U.S. Appl. No. 15/479,256 dated Feb. 4, 2019, 7 pages.
International Search Report and Written Opinion for PCT Appl. Ser. No. PCT/US2018/041411 dated Feb. 8, 2019, 13 pages.
Schonfeld, "Optical readout of single spins for quantum computing and magnetic sensing", Dissertation, Fachbereich Physlk der Freien Universitat Berlin, May 1, 2011, 21 Pages. (relevant pages only), XP055143403. Retrieved from the Internet: URL: http://www.dlss.fu-berlln.de/diss/servlets/MCRFIleNodeServleUFU DISS_derivate_00000001219 9/DIssertatIon_Slmon-choenfela_PublIcVersion-2.pdfJsessionid-89A943688E59.
U.S. Final Office Action for U.S. Appl. No. 15/003,396 dated Mar. 22, 2019, 13 pages.
U.S. Final Office Action for U.S. Appl. No. 15/382,045 dated Apr. 26, 2019, 16 pages.
U.S. Final Office Action for U.S. Appl. No. 15/443,422 dated Mar. 7, 2019, 17 pages.
U.S. Non-Final Office Action for U.S. Appl. No. 15/003,193 dated Apr. 11, 2019, 7 pages.
U.S. Non-Final Office Action for U.S. Appl. No. 15/003,309 dated Feb. 13, 2019, 16 pages.
U.S. Non-Final Office Action for U.S. Appl. No. 15/003,617 dated Feb. 26, 2019, 10 pages.
U.S. Non-Final Office Action for U.S. Appl. No. 15/372,201 dated Apr. 2, 2019, 10 pages.
U.S. Non-Final Office Action for U.S. Appl. No. 15/419,832 dated Feb. 8, 2019, 12 pages.
U.S. Non-Final Office Action for U.S. Appl. No. 15/440,194 dated Feb. 15, 2019, 21 pages.
U.S. Non-Final Office Action for U.S. Appl. No. 15/446,373 dated Apr. 19, 2019, 8 pages.
U.S. Non-Final Office Action for U.S. Appl. No. 15/468,314 dated Mar. 28, 2019, 17 pages.
U.S. Non-Final Office Action for U.S. Appl. No. 15/468,410 dated Apr. 11, 2019, 15 pages.
U.S. Non-Final Office Action for U.S. Appl. No. 15/468,559 dated Apr. 11, 2019, 12 pages.
U.S. Non-Final Office Action for U.S. Appl. No. 15/469,374 dated Feb. 28, 2019, 14 pages.
U.S. Notice of Allowance for U.S. Appl. No. 15/003,617 dated Apr. 30, 2019, 9 pages.
U.S. Notice of Allowance for U.S. Appl. No. 15/207,457 dated Mar. 6, 2019, 16 pages.
U.S. Notice of Allowance for U.S. Appl. No. 15/376,244 dated Feb. 21, 2019, 7 pages.
U.S. Notice of Allowance for U.S. Appl. No. 15/380,419 dated Feb. 26, 2019, 5 pages.
U.S. Notice of Allowance for U.S. Appl. No. 15/400,794 dated Apr. 25, 2019, 5 pages.
U.S. Notice of Allowance for U.S. Appl. No. 15/437,038 dated Mar. 21, 2019, 13 pages.
U.S. Notice of Allowance for U.S. Appl. No. 15/468,282 dated Feb. 19, 2019, 8 pages.
U.S. Notice of Allowance for U.S. Appl. No. 15/468,356 dated Apr. 22, 2019, 8 pages.
U.S. Notice of Allowance for U.S. Appl. No. 15/468,582 dated Mar. 21, 2019, 13 pages.
U.S. Notice of Allowance for U.S. Appl. No. 15/468,951 dated Mar. 28, 2019, 8 pages.

US 10,371,765 B2

GEOLOCATION OF MAGNETIC SOURCES USING VECTOR MAGNETOMETER SENSORS

CROSS-REFERENCE TO RELATED PATENT APPLICATIONS

The present application claims the benefit of priority from U.S. Provisional Patent Application No. 62/360,940, filed Jul. 11, 2016, which is incorporated herein by reference in its entirety.

BACKGROUND

The present disclosure generally relates to the field of magnetometers, including for example methods and systems for geolocating magnetic sources using vector magnetometer sensors.

SUMMARY

Some embodiments relate to a system including one or more diamond nitrogen vacancy (DNV) sensors and a controller. The controller can be configured to activate the DNV sensors, receive a set of vector measurements from the DNV sensors, and determine an angle of a magnetic source relative to the one or more DNV sensors based on the received set of vector measurements from the DNV sensors. In other implementations, the controller may be configured to determine geolocation of a magnetic source relative to the one or more DNV sensors based on the received set of vector measurements from the DNV sensors.

Another embodiment relates to a geolocating device that includes one or more diamond nitrogen vacancy (DNV) sensors and means for activating the DNV sensors, receiving a set of vector measurements from the DNV sensors, and determining an angle of a magnetic source relative to the one or more DNV sensors based on the received set of vector measurements from the DNV sensors.

DETAILED DESCRIPTION

It is possible to resolve a magnetic field vector from a diamond nitrogen vacancy magnetic field sensor. In some implementations, two or more vector magnetometers may be used to resolve a position of a magnetic source. In some further implementations, a position and dipole of a magnetic source may be determined using three or more sensors. In some embodiments, magnetic sources may be geolocated using bilateration and/or vector search algorithms. Sources may be intentional or unintentional, may be passive (e.g., perturbations to Earth's geomagnetic field) or active, and may include DC, AC, or slowly varying magnetic fields. Potential applications include DNV calibration, Magnetic Anomaly Detection (MAD), industrial inventory management, magnetic beacon based applications, PNT (Position, Navigation and Timing).

NV Center, its Electronic Structure, and Optical and RF Interaction

Figure 1:
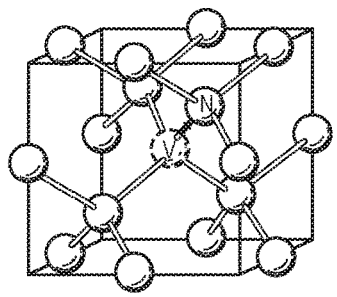
FIG. 1 illustrates one orientation of a nitrogen vacancy (NV) center in a diamond lattice.

The nitrogen vacancy (NV) center in diamond comprises a substitutional nitrogen atom in a lattice site adjacent a carbon vacancy as shown in FIG. 1. The NV center may have four orientations, each corresponding to a different crystallographic orientation of the diamond lattice.

The NV center may exist in a neutral charge state or a negative charge state. The neutral charge state uses the nomenclature $NV^0$, while the negative charge state uses the nomenclature NV.

The NV center has a number of electrons including three unpaired electrons, each one from the vacancy to a respective of the three carbon atoms adjacent to the vacancy, and a pair of electrons between the nitrogen and the vacancy. The NV center, which is in the negatively charged state, also includes an extra electron.

Figure 2:
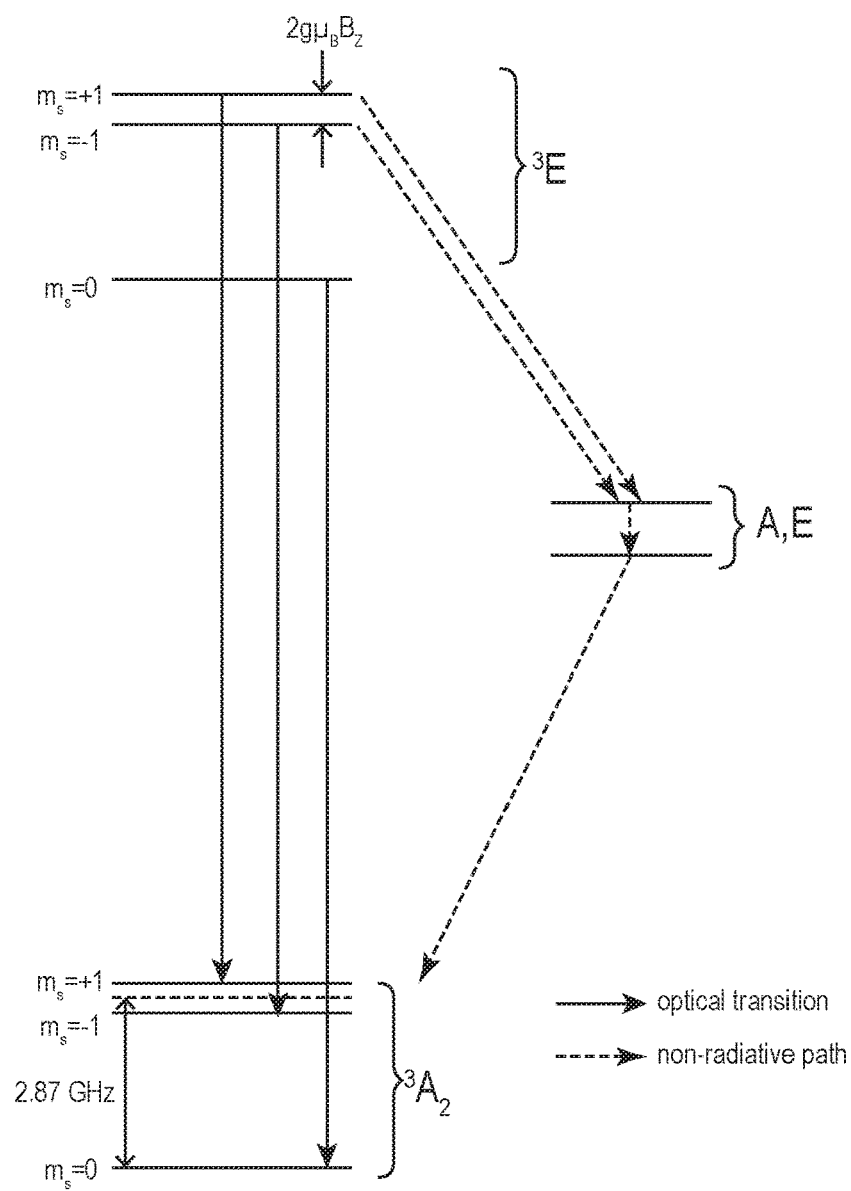
FIG. 2 is an energy level diagram that illustrates energy levels of spin states for the NV center.

The NV center has rotational symmetry, and as shown in FIG. 2, has a ground state, which is a spin triplet with $^3A_2$ symmetry with one spin state $m_s=0$, and two further spin states $m_s=+1$, and $m_s=-1$. In the absence of an external magnetic field, the $m_s=\pm 1$ energy levels are offset from the $m_s=0$ due to spin-spin interactions, and the $m_s=\pm 1$ energy levels are degenerate, i.e., they have the same energy. The $m_s=0$ spin state energy level is split from the $m_s=\pm 1$ energy levels by a energy of 2.87 GHz for a zero external magnetic field.

Introducing an external magnetic field with a component along the NV axis lifts the degeneracy of the $m_s=\pm 1$ energy levels, splitting the energy levels $m_s=\pm 1$ by an amount $2g\mu_B Bz$, where g is the g-factor, $\mu_B$ is the Bohr magneton, and Bz is the component of the external magnetic field along the NV axis. This relationship is correct to a first order and inclusion of higher order corrections is a straightforward matter and should not materially affect the computational and logic steps.

The NV center electronic structure further includes an excited triplet state $^3E$ with corresponding $m_s=0$ and $m_s=\pm 1$ spin states. The optical transitions between the ground state $^3A_2$ and the excited triplet $^3E$ are predominantly spin conserving, meaning that the optical transitions are between initial and final states which have the same spin. For a direct transition between the excited triplet $^3E$ and the ground state $^3A_2$, a photon of red light is emitted with a photon energy corresponding to the energy difference between the energy levels of the transitions.

An alternate non-radiative decay route from the triplet $^3E$ to the ground state $^3A_2$ via intermediate electron states exists, in which the intermediate states are thought to be intermediate singlet states A, E with intermediate energy levels. The transition rate from the $m_s=\pm 1$ spin states of the excited triplet $^3E$ to the intermediate energy levels is significantly greater than that from the $m_s=0$ spin state of the excited triplet $^3E$ to the intermediate energy levels. The transition from the singlet states A, E to the ground state triplet $^3A_2$ predominantly decays to the $m_s=0$ spin state over the $m_s=\pm1$ spin states. These features of the decay from the excited triplet $^3E$ state via the intermediate singlet states A, E to the ground state triplet $^3A_2$ allows that if optical excitation is provided to the system, the optical excitation will eventually pump the NV center into the $m_s=0$ spin state of the ground state $^3A_2$. In this way, the population of the $m_s=0$ spin state of the ground state $^3A_2$ may be reset to a maximum (e.g., greatest or near greatest) polarization determined by the decay rates from the triplet $^3E$ to the intermediate singlet states.

Another feature of the decay is that the fluorescence intensity due to optically stimulating the excited triplet $^3E$ state is less for the $m_s=\pm1$ states than for the $m_s=0$ spin state. This is so because the decay via the intermediate states does not result in a photon emitted in the fluorescence band, and because of the greater probability that the $m_s=\pm1$ states of the excited triplet $^3E$ state will decay via the non-radiative decay path. The lower fluorescence intensity for the $m_s=\pm1$ states than for the $m_s=0$ spin state allows the fluorescence intensity to be used to determine the spin state. As the population of the $m_s=\pm1$ states increases relative to the $m_s=0$ spin, the overall fluorescence intensity will be reduced.

NV Center, or Magneto-Optical Defect Center, Magnetic Sensor System

Figure 3:
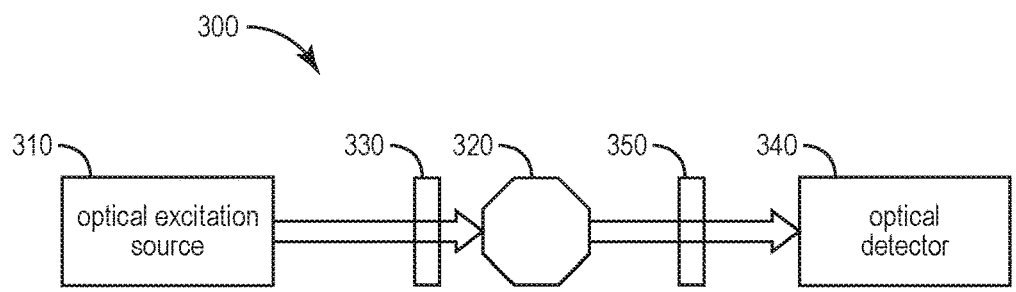
FIG. 3 is a schematic illustrating an NV center magnetic sensor system.

FIG. 3 is a schematic illustrating a NV center magnetic sensor system 300 which uses fluorescence intensity to distinguish the $m_s=\pm1$ states, and to measure the magnetic field based on the energy difference between the $m_s=+1$ state and the $m_s=-1$ state. The system 300 includes an optical excitation source 310, which directs optical excitation to an NV diamond material 320 with NV centers. The system 300 further includes an RF excitation source 330 which provides RF radiation to the NV diamond material 320. Light from the NV diamond may be directed through an optical filter 350 to an optical detector 340.

The RF excitation source 330 may be a microwave coil, for example. The RF excitation source 330 when emitting RF radiation with a photon energy resonant with the transition energy between ground $m_s=0$ spin state and the $m_s=+1$ spin state excites a transition between those spin states. For such a resonance, the spin state cycles between ground $m_s=0$ spin state and the $m_s=+1$ spin state, reducing the population in the $m_s=0$ spin state and reducing the overall fluorescence at resonance. Similarly resonance occurs between the $m_s=0$ spin state and the $m_s=-1$ spin state of the ground state when the photon energy of the RF radiation emitted by the RF excitation source is the difference in energies of the $m_s=0$ spin state and the $m_s=-1$ spin state. At resonance between the $m_s=0$ spin state and the $m_s=-1$ spin state, or between the $m_s=0$ spin state and the $m_s=+1$ spin state, there is a decrease in the fluorescence intensity.

The optical excitation source 310 may be a laser or a light emitting diode, for example, which emits light in the green, for example. The optical excitation source 310 induces fluorescence in the red, which corresponds to an electronic transition from the excited state to the ground state. Light from the NV diamond material 320 is directed through the optical filter 350 to filter out light in the excitation band (in the green for example), and to pass light in the red fluorescence band, which in turn is detected by the detector 340. The optical excitation light source 310, in addition to exciting fluorescence in the diamond material 320, also serves to reset the population of the $m_s=0$ spin state of the ground state $^3A_2$ to a maximum polarization, or other desired polarization.

Figure 4:
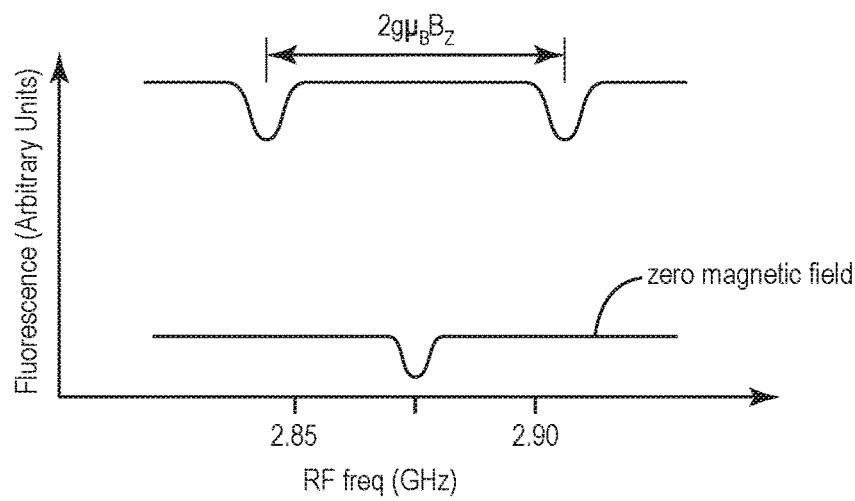
FIG. 4 is a graph illustrating the fluorescence as a function of applied RF frequency of an NV center along a given direction for a zero magnetic field and a non-zero magnetic field.

For continuous wave excitation, the optical excitation source 310 continuously pumps the NV centers, and the RF excitation source 330 sweeps across a frequency range which includes the zero splitting (when the $m_s=\pm1$ spin states have the same energy) photon energy of 2.87 GHz. The fluorescence for an RF sweep corresponding to a diamond material 320 with NV centers aligned along a single direction is shown in FIG. 4 for different magnetic field components Bz along the NV axis, where the energy splitting between the $m_s=-1$ spin state and the $m_s=+1$ spin state increases with Bz. Thus, the component Bz may be determined. Optical excitation schemes other than continuous wave excitation are contemplated, such as excitation schemes involving pulsed optical excitation, and pulsed RF excitation. Examples, of pulsed excitation schemes include Ramsey pulse sequence, and spin echo pulse sequence.

Figure 5:
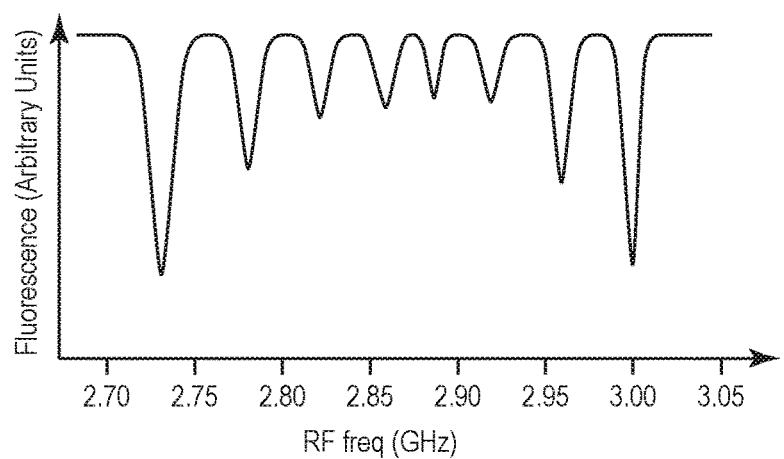
FIG. 5 is a graph illustrating the fluorescence as a function of applied RF frequency for four different NV center orientations for a non-zero magnetic field.

In general, the diamond material 320 will have NV centers aligned along directions of four different orientation classes. FIG. 5 illustrates fluorescence as a function of RF frequency for the case where the diamond material 320 has NV centers aligned along directions of four different orientation classes. In this case, the component Bz along each of the different orientations may be determined. These results along with the known orientation of crystallographic planes of a diamond lattice provide not only the magnitude of the external magnetic field to be determined, but also the direction of the magnetic field.

While FIG. 3 illustrates an NV center magnetic sensor system 300 with NV diamond material 320 with a plurality of NV centers, in general the magnetic sensor system may instead employ a different magneto-optical defect center material, with a plurality of magneto-optical defect centers. The electronic spin state energies of the magneto-optical defect centers shift with magnetic field, and the optical response, such as fluorescence, for the different spin states is not the same for all of the different spin states. In this way, the magnetic field may be determined based on optical excitation, and possibly RF excitation, in a corresponding way to that described above with NV diamond material.

Figure 6:
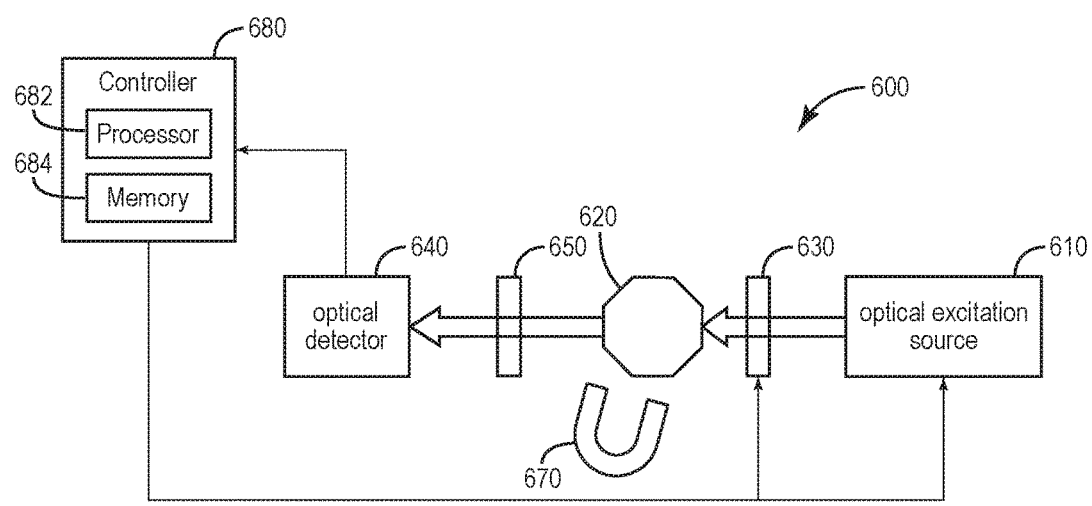
FIG. 6 is a schematic illustrating an NV center magnetic sensor system according to some embodiments.

FIG. 6 is a schematic of an NV center magnetic sensor 600, according to some embodiments. The sensor 600 includes an optical excitation source 610, which directs optical excitation to an NV diamond material 620 with NV centers, or another magneto-optical defect center material with magneto-optical defect centers. An RF excitation source 630 provides RF radiation to the NV diamond material 620. The NV center magnetic sensor 600 may include a bias magnet 670 applying a bias magnetic field to the NV diamond material 620. Light from the NV diamond material 620 may be directed through an optical filter 650 and an electromagnetic interference (EMI) filter 660, which suppresses conducted interference, to an optical detector 640. The sensor 600 further includes a controller 680 arranged to receive a light detection signal from the optical detector 640 and to control the optical excitation source 610 and the RF excitation source 630.

The RF excitation source 630 may be a microwave coil, for example. The RF excitation source 630 is controlled to emit RF radiation with a photon energy resonant with the transition energy between the ground $m_s=0$ spin state and the $m_s=\pm1$ spin states as discussed above with respect to FIG. 3.

The optical excitation source 610 may be a laser or a light emitting diode, for example, which emits light in the green, for example. The optical excitation source 610 induces fluorescence in the red, which corresponds to an electronic transition from the excited state to the ground state. Light from the NV diamond material 620 is directed through the optical filter 650 to filter out light in the excitation band (in the green for example), and to pass light in the red fluorescence band, which in turn is detected by the optical detector 640. The EMI filter 660 is arranged between the optical filter 650 and the optical detector 640 and suppresses conducted interference. The optical excitation light source 610, in addition to exciting fluorescence in the NV diamond material 620, also serves to reset the population of the $m_s=0$ spin state of the ground state $^3A_2$ to a maximum polarization, or other desired polarization.

The controller 680 is arranged to receive a light detection signal from the optical detector 640 and to control the optical excitation source 610 and the RF excitation source 630. The controller may include a processor 682 and a memory 684, in order to control the operation of the optical excitation source 610 and the RF excitation source 630. The memory 684, which may include a nontransitory computer readable medium, may store instructions to allow the operation of the optical excitation source 610 and the RF excitation source 630 to be controlled.

According to some embodiments of operation, the controller 680 controls the operation such that the optical excitation source 610 continuously pumps the NV centers of the NV diamond material 620. The RF excitation source 630 is controlled to continuously sweep across a frequency range which includes the zero splitting (when the $m_s=\pm1$ spin states have the same energy) photon energy of 2.87 GHz. When the photon energy of the RF radiation emitted by the RF excitation source 630 is the difference in energies of the $m_s=0$ spin state and the $m_s=-1$ or $m_s=+1$ spin state, the overall fluorescence intensity is reduced at resonance, as discussed above with respect to FIG. 3. In this case, there is a decrease in the fluorescence intensity when the RF energy resonates with an energy difference of the $m_s=0$ spin state and the $m_s=-1$ or $m_s=+1$ spin states. In this way the component of the magnetic field Bz along the NV axis may be determined by the difference in energies between the $m_s=-1$ and the $m_s=+1$ spin states.

As noted above, the diamond material 620 will have NV centers aligned along directions of four different orientation classes, and the component Bz along each of the different orientations may be determined based on the difference in energy between the $m_s=-1$ and the $m_s=+1$ spin states for the respective orientation classes. In certain cases, however, it may be difficult to determine which energy splitting corresponds to which orientation class, due to overlap of the energies, etc. The bias magnet 670 provides a magnetic field, which is preferably uniform on the NV diamond material 620, to separate the energies for the different orientation classes, so that they may be more easily identified.

Systems and Methods for Angle Determination and/or Geolocating Magnetic Sources

The NV center magnetic sensor is capable of resolving a vector of a magnetic source. High sensitivity, high bandwidth, full vector magnetometry sensing may be provided by a set of DNV sensors to estimate the location of a fixed magnetic source with known dipole orientation, the location and dipole orientation of a fixed magnetic source with unknown dipole orientation, the location of an AC magnetic source with fixed dipole orientation, and/or the location of a rotating dipole magnetic source with known plane of rotation relative to sensors. Alternatively to the dipole orientation being known, the dipole moment and position may be determined using the sensing.

To determine the geolocation of the magnetic source, a controller receives the vector measurement inputs from two or more of the magnetometers and computes a score function and associated gradient for candidate magnetic source locations and orientations based on the magnetic fields as measured at a set of spatially distributed (DNV) vector magnetometer sensors. In some implementations, the controller can be applied to locate DC or AC magnetic sources. The system utilizes the vector difference between sensors as a means of mitigating common-mode spatially flat interfering sources and/or the full vector estimates from each sensor to provide more degrees of freedom to estimate the source location and orientation.

In some systems, an array of magnetometers measuring only scalar values utilizes Anderson functions to perform certain Magnetic Anomaly Detection (MAD) tasks. Anderson functions describe how a magnetic field amplitude and gradient of the full field amplitude vary as a function of relative geometry with respect to a magnetic source or disturbance. In such Anderson scalar systems, the array of scalar measurements may be compared to expected Anderson function values for a guessed location of magnetic source through trial and error. Such systems require a large array of sensors covering a large area and multiple iterative guesses to determine the location of the magnetic source. In other systems, a geolocation magnetic sensor may use a three-dimensional magnetic sensor and a multi-axis gradiometer with direct inversion of a 1st order expansion formula to provide a closed form solution for location of an RFID tag. Such a sensor consists of three orthogonal loop coils, three orthogonal planar gradiometers and three orthogonal axial gradiometers, thus requiring a large and complex sensor apparatus with limited sensitivity. Moreover, for the orthogonal loops of wire, the magnetic field detection is limited to AC fields for inducing current within the looped coils.

In contrast, the solution presented herein can minimize the number of magnetometers needed and reduce the spatial area needed to perform magnetic source geolocation. In particular, the instantaneous vector DNV sensors provide high bandwidth and can utilize dipole field matching to geolocate a magnetic source. Such DNV sensors provide a higher sensitivity and can provide vector estimation in a single compact sensor. In some implementations, improvements in the DNV sensitivity and 1/f noise compensation allow extension of geolocation to DC, slowly varying AC, and higher frequency AC tones. Low frequency AC sources offer particular potential benefits in salt-water environments where suppression of magnetic fields increases with frequency. In some embodiments described herein, the geolocation with full vector magnetometers offers improved capability over scalar full-field magnetometers and/or associated full field sensors and gradiometers. Potential incorporation of multiple vector DNV sensors permits full three by three Jacobian (gradient matrix) computation from 4 compact sensors.

Figure 7:
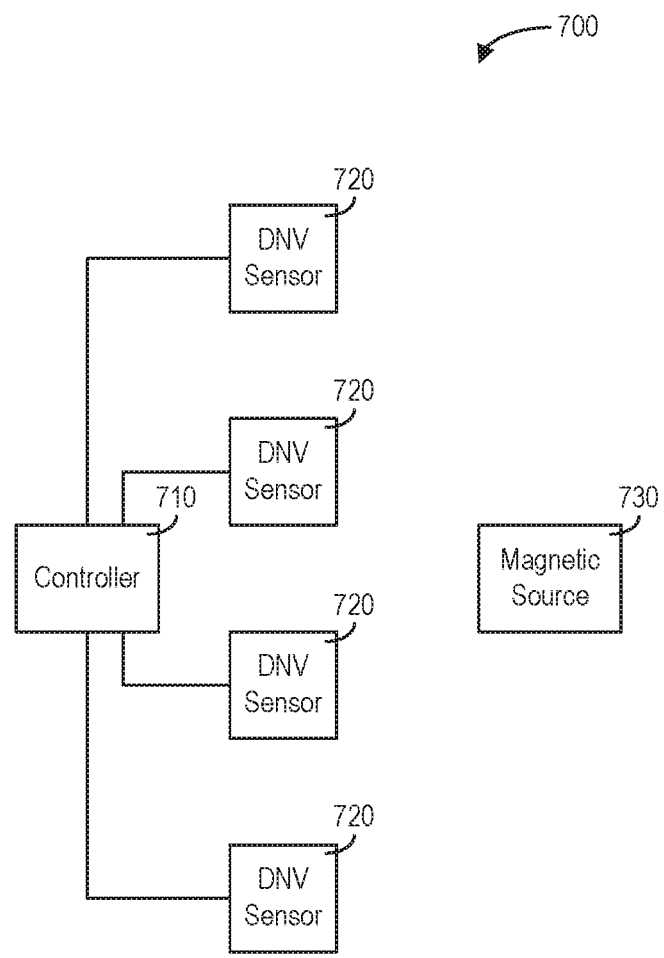
FIG. 7 is a schematic illustrating a controller and several DNV sensors for detecting an angle and/or position of a magnetic source relative to the DNV sensors.

Referring to the system of FIG. 7, four DNV sensors 720, such as those described above in reference to FIGS. 1-6, are shown coupled to a controller 710 and positioned relative to a magnetic source. The controller 710, in addition to controlling the DNV sensors 720 and receiving data from the sensors 720, may perform data processing on the data. In this regard, the controller 710 may include a subcontroller to control and receive data from the sensors 720, and one or more further subcontroller to perform data processing on the data. Each of the DNV sensors 720 takes multiple measurements over time and/or can take a single measurement during the same time window. In some implementations, the controller 710 may have the set of DNV sensors 720 take an initial measurement with no magnetic source 730 present to provide a base measurement such that a variation in the measurement from the DNV sensors 720 can be detected when a magnetic source 730 is present. That is, the controller 710 may store a base magnetic field measurement to compare to subsequent measurements from the DNV sensors 720. Subsequent measurements can be compared to the base measurement to detect the presence of a magnetic source 730. In some implementations, the earth's magnetic field and/or the background magnetic field can change over time. Thus, in some instances, if there are relatively minor differences between the base measurement and the subsequent measurement, this may be due to changes in the earth's magnetic field. Accordingly, in some implementations, it may be determined that the magnetic source 730 is present if the differences between the base measurement and the subsequent measurement is larger than a threshold amount. The threshold amount can be large enough that changes from the base measurement to the subsequent measurement caused by the changes in the earth's magnetic field are ignored, but small enough that changes caused by the presence or movement of a magnetic source are larger than the threshold amount. Using the subsequent measurement, a plane angle and/or a geolocation for the magnetic source 730 can be determined.

In some implementations, the DNV sensors 720 each take a measurement of a magnetic field once per second. The controller 710 can receive vector magnetic measurements taken by the DNV sensors 720. In some implementations, the measurements are received simultaneously from the DNV sensors 720. The controller 710 receives each of the measurements and stores them as sets of measurements. The most recently received set of measurements can be compared to the previously received set of measurements. As a magnetic source 730 moves closer or moves around when in detection range, the magnetic source disrupts the magnetic field detected by the DNV sensors 720. The DNV sensors 720 may be distributed in any geometric configuration and the magnetic field at the points detected by the DNV sensors 720 may be affected differently based on the location of the magnetic source 730.

In an illustrative embodiment, the plane angle, size, and/or location of a rotating magnetic source can be determined based on the measurements from the DNV sensors. For plane angle estimation relative to the DNV sensors:

$$M = A^T R_{r2D} B + W$$

where $W \sim (NCO, I)$, $R_{r2D}$ is the transform of the positional coordinates of a room or area to the diamond, and B is the detected magnetic field. For a rotating magnetic source in the same plane as a DNV sensor and with a rotation axis along the z-axis of the area and a moment in the X-Y plane of the area with a plane angle of $\theta$, then the magnetic field, B, can be defined as:

$$B = R_\theta \begin{bmatrix} 2\cos(\omega t + \varphi) \\ \sin(\omega t + \varphi) \\ 0 \end{bmatrix}$$

where $\varphi$ is an unknown phase offset and $t=[t_1, t_2, \ldots, t_n]$ is the time vector. Thus, $$M = A^T R_{r2D} R_\theta \begin{bmatrix} 2\cos(\omega t + \varphi) \\ \sin(\omega t + \varphi) \\ 0 \end{bmatrix} + W$$

Converting the cosine and sine terms using Euler's formula, $$M = A^T R_{r2D} R_\theta \begin{bmatrix} e^{i\varphi}e^{i\omega t} + e^{-i\varphi}e^{-i\omega t} \\ \frac{1}{2}e^{i\varphi}e^{i\omega t} - \frac{1}{2}e^{-i\varphi}e^{-i\omega t} \\ 0 \end{bmatrix} + W$$

which be further reduced to $$M = A^T R_{r2D} R_\theta E + W$$

Given a known M, $R_{r2D}$, and A values, then $\hat{\theta}$ can be determined since $\frac{3}{4}AA^T = I$. Accordingly, $$\frac{3}{4} R_\theta^T R_{r2D}^T AM = E + W'$$

To determine the $\hat{\theta}$ according to a first implementation, the controller can perform matched filtering against the $e^{i\omega t}$ term to determine the $R_\theta$ transform that maximizes the x-component. Thus, the controller can calculate:

$$R_{\hat{\theta}} = \underset{R_\theta}{\text{argmax}} \left| \frac{3}{4} R_\theta^T R_{r2D}^T AM(e^{i\omega t})^H \right|$$

where $(e^{i\omega t})^H$ is the conjugate transpose and $R_\theta^T R_{r2D} AM (e^{i\omega t})^H$ is a three by one vector that can be obtained directly from Fast Fourier Transform.

In some implementations, the amplitude ratio between a dominant direction and a perpendicular direction of the dipole can be leveraged and the ninety degree phase offset can also be used. That is, $$R_{\hat{\theta}} = \underset{R_\theta}{\text{argmax}} \left| [2 - i0] \frac{3}{4} R_{r2D}^T R_\theta^T AM(e^{i\omega t})^H \right|$$

In yet a further implementation, an Orthogonal Procrustes algorithm can be used by the controller to determine the $R_\theta$ that minimizes $$\left\| R_\theta E - \frac{3}{4} R_{r2D}^T AM \right\|_F$$

In further implementations, the DNV sensors 720 and the controller 710 can be used for geolocation through dipole field matching. That is, the vector measurements of the DNV sensors 720 of the magnetic source 730 can be compared to a set of known orientations and/or configurations for a dipole magnetic source. In some implementations, a time series of vector measurements can be compared to a time series of known orientations and/or configurations for a dipole magnetic source. The controller 720, via a subcontroller for example, can compare the vector measurements to the set of known orientations and/or configurations for a dipole magnetic source to determine the maximum (e.g., greatest or near greatest). The maximum orientation and/or configuration is then set as the geolocation and/or orientation of the magnetic source 730 relative to the DNV sensors 720. By comparing the vector measurements to known orientations and/or configurations of magnetic sources, a direct determination of the angle of the dipole magnetic source and/or location can be determined.

In an example implementation, five DNV sensors 720 may be used with the controller 710 to determine a geolocation of a magnetic source and associated moment vector from the resulting vector magnetic field measured by the five DNV sensors 720. Other numbers of DNV sensors 720 may also be used, such as two or three. The controller 710 is electrically coupled to the five DNV sensors 720 to receive data from the DNV sensors. In some implementations, the controller 710, which may include one or more subcontrollers, may be in data communication with a DNV sensor controller to receive vector data from the DNV sensor controller. In other implementations, the controller 710 may be in direct data communication with the DNV sensors 720 to receive raw data output. The controller 710 can include an initial position vector for the DNV sensors 720, such as [X_coord, Y_coord, Z_coord] defining each DNV sensor location.

The example implementation may also generate a Monte Carlo set of dipole data based on an approximation of a single magnetic source. The controller 710 can include an upper bound and lower bound vector defining an upper position and lower position boundary for the Monte Carlo set of dipole data for the approximated single magnetic source relative to the DNV sensors 720. In some implementations, the controller 710 may also store an initial start position for generating the Monte Carlo set of dipole data for the approximated single magnetic source. The initial start position may be randomly generated positional X, Y, and Z coordinates and/or may be static X, Y, and Z values. The approximated single magnetic source may include a static dipole moment.

To generate the Monte Carlo set, the controller 710 is configured to define three by one vectors for each magnetic field and corresponding gradients that would be detected by each DNV sensor for the approximated single magnetic source, such as [SensorField#, SensorFieldGradientX, SensorFieldGradientY, SensorFieldGradientZ], which is determined as a function of the sensor position, a position of the approximated single magnetic source, and the dipole moment. A Monte Carlo method can be performed for a given root mean square (RMS) noise per vector component. A geolocation function generates data for the approximated single magnetic source and estimated dipole moment based on the sensor positions, the measured resultant magnetic field at each sensor with Monte Carlo generated RMS noise per vector component, the upper and lower bounds, and the initial start position. The geolocation function also generates data for a measured magnetic source based on the measured magnetic vectors of the DNV sensors 720, the sensor positions, the dipole moment, an initial dipole position estimate, and an upper bound and a lower bound for the dipole position. That is, the geolocation function may utilize the magnetic field data from the DNV sensors to determine a position and dipole moment of the magnetic source based on dipole field matching.

In some implementations, the initial dipole position estimate and dipole moment vector estimate may be modified based on a scoring function based on an error fit between the estimated position and moment of the magnetic source and the measured dipole magnetic fields by the DNV sensors. In some implementations, a least squares algorithm may be used to perform a constrained least squares fit to optimize performance. Below is provided exemplary computer code (MATLAB

```
% ===========================================================================
% Script to evaluate magnetic field from a dipole at five sensors.
% ===========================================================================
%%% Initialization
clear;
%%% Define grid points
% X = Right on monitor, Y = Up on monitor, Z = Out of monitor towards user.
%%% Define Sensor Locations:
sensor1Location = [-10 0 1]';   % (3 x 1) (m)
sensor2Location = [0 0 1]';     % (3 x 1) (m)
sensor3Location = [10 0 1]';    % (3 x 1) (m)
sensor4Location = [-5 5 1.5]';  % (3 x 1) (m)
sensor5Location = [5 5 1.5]';   % (3 x 1) (m)
sensorPos = [sensor1Location, sensor2Location, sensor3Location, ...
        sensor4Location, sensor5Location];
%%% Define initial estimates and bounds for search algorithm:
% Define initial dipole position and moment estimates as well as associated
% upper and lower search bounds for the position and moment estimates
MC_initPosMoment = [0, 20, 1, 10, 10, 10];
MC_posMomentLowerBound = [-80, -15, 0, -100, -100, -100];
MC_posMomentUpperBound = [ 80, 100, 2, 100, 100, 100];
%%% Define Test Dipole Moment and Position:
% %  Define Magnet Test Location for analysis
testDipolePosition = [9, 15, 1.25 ]
% %  Define Magnet Dipole magnitude and orientation for analysis
dipoleMoment = 63.8 * unit([1 1 1]) % (3 x 1) (T)
%%% Specify RMS noise (per magnetic field component)
noise_nT = 0.1 % Gaussian b field error (nT) per xyz component
%%% Generate truth data for all sensor locations
[ sensorField, ...
        sensorFieldGradX, sensorFieldGradY, sensorFieldGradZ ] =...
        dipoleBField_wDipolePosGradient_SingleDipole(...
        sensorPos, testDipolePosition', dipoleMoment');% [ sensor1Field, ...
measuredB = 1e9*sensorField;
measuredBfield_mag_nT = sqrt(sum(measuredB.^2,1))
%%% Run Monte Carlo for given RMS noise per vector component
nMonteCarloTrials = 40;
for ii = 1:nMonteCarloTrials,
```

```
    MCmeasB = measuredB + noise_nT*randn(size(measuredB));
    % Call Geolocation solver:
    [ magnet3dPosMoment (ii,:) ] = xyzGeolocateBfield_wDipole_multiBfit( ...
        MCmeasB, ...
        sensorPos, ...
        MC_initPosMoment, MC_posMomentLowerBound, MC_posMomentUpperBound);
end
%% Compute sample Monte Carlo statistics on the accuracy of the target
% dipole position and moment estimates:
meanMCdipolePos = mean(magnet3dPosMoment(:,1:3),1)
meanMCdipoleMoment = mean(magnet3dPosMoment(:,4:6),1)
MCdipolePosErr = magnet3dPosMoment(:,1:3)-...
    repmat(testDipolePosition,nMonteCarloTrials,1);
MCdipoleMomentErr = magnet3dPosMoment(:,4:6)-...
    repmat(dipoleMoment,nMonteCarloTrials,1);
meanMCdipolePosErr = mean(MCdipolePosErr,1)
meanMCdipoleMomentErr = mean(MCdipoleMomentErr,1)
stdMCdipolePosErr = std(MCdipolePosErr,1)
stdMCdipoleMomentErr = std(MCdipoleMomentErr,1)
rmsMCdipolePosErr = rms(MCdipolePosErr,1)'
rmsMCdipoleMomentErr = rms(MCdipoleMomentErr,1)'
%% End of Monte Carlo Geolocation Script
% =====================================================================
% Function to estimate magnetic dipole position and moment vector from
% measurements of the resulting magnetic field at multiple sensors.
% =====================================================================
function [ magnet3dPosMoment ] = xyzGeolocateBfield_wDipole_multiBfit( ...
    measBvec, ...
    sensorPos, ...
    dipolePosXYZMomentXYZ_init, ...
    dipolePosXYZMomentXYZ_LB, dipolePosXYZMomentXYZ_UB)
% xyzGeolocateBfield_wDipole_multiBfit.m
%   Function estimates the geolocation and moment of a magnetic dipole
%   target from measured estimates of the magnetic field caused by the
%   dipole source at a set of known sensor positions (and orientations).
% Define geolocation score function to be optimized:
geoScoreFunWrapper = @(dipolePosXYZMomentXYZ)
geoDipoleErrorFun6stateFitXYZDipole( ...
    dipolePosXYZMomentXYZ(1:3), ...
    measBvec, ...
    sensorPos, dipolePosXYZMomentXYZ(4:6)' );
% If upper and lower bounds are not provided in the function, the following
% commands provide representative bounds for an envisioned scenario.
if (nargin < 5)
    dipolePosXYZMomentXYZ_UB = [ 2,3,2, 100, 100, 100];
end
if (nargin < 4)
    dipolePosXYZMomentXYZ_LB = [-2,1,0, -100, -100, -100];
end
% If an initial position and dipole moment estimate is not provided, the
% following commands provide a representative initial estimate for an
% envisioned scenario.
if (nargin < 3)
    dipolePosXYZMomentXYZ_init = [0,2,1, 1, 1, 1];
end
% Perform optimization using built-in lsqnonlin algorithm to perform
% constrained ordinary least squares
%   Set options for contrained nonlinear least square solver:
options = optimoptions ('lsqnonlin', ...
    'TolX', 1e-16, 'TolFun', 1e-16, ...
    'MaxFunEvals', 4000, 'MaxIter', 1000, 'Display', 'off', ...
    'Jacobian','on');
%   Call nonlinear least squares solver:
[magnet3dPosMoment, ~] = lsqnonlin( geoScoreFunWrapper, ...
    dipolePosXYZMomentXYZ_init, ...
    dipolePosXYZMomentXYZ_LB, dipolePosXYZMomentXYZ_UB, options);
end
% =====================================================================
% Function to compute the error between a set of measured magnetic field
% vectors at known sensor locations and the expected magnetic field at the
% same locations for a candidate dipole moment and position.
% =====================================================================
function [multiBerror, multiBJacobian] = ...
    geoDipoleErrorFun6stateFitXYZDipole( dipolePosXYZ, ...
    measBvec, sensorPos, dipoleMoment )
    % Function call computes the error between a set of measured magnetic
    % field vectors, "measBvec" and the expected magnetic fields for a scenario
    % described by sensors at position "sensorPos" and magnetic dipole sources
    % with moments "dipoleMoment" located at positions "dipolePosXYZ".
```

```
% The function call further calculates the Jacobian matrix associated with
% the given error function.
% Compute the resulting magnetic field at a given sensor Position for a
% dipole at given position with given dipole moment
[ sensorField, ...
        sensorFieldGradX, sensorFieldGradY, sensorFieldGradZ, ...
        sensorFieldGrad_mX, sensorFieldGrad_mY, sensorFieldGrad_mZ ] = ...
        dipoleBField_wDipolePosVecGradient_SingleDipole(...
        sensorPos, dipolePosXYZ', dipoleMoment);
% Compute the error function between the measured and expected magnetic
% fields at the given sensor locations due to the specified candidate set
% of dipole positions and moments.
multiBerror = [measBvec - 1e9*sensorField];
% Calculate Jacobian matrix:
if nargout > 1
    Jacobian = zeros(1,length(dipolePosXYZ));
    multiBJacobian = -1e9*[ ...
        sensorFieldGradX(:), sensorFieldGradY(:), sensorFieldGradZ(:), ...
        sensorFieldGrad_mX(:), sensorFieldGrad_mY(:), sensorFieldGrad_mZ(:) ];
end
end
% ==========================================================================
% Function to compute the magnetic field and corresponding gradient vectors
% at specified sensor positions based upon a magnetic dipole with specified
% moment and position.
%
% USAGE
%   [bField, bFieldGradX, bFieldGradY, bFieldGradZ] = ...
%       dipoleBField_wDipolePosGradient(sPos,dPos,m,mu)
% INPUTS
%   sPos - the sensor position (3x1 or 3xN column) vector
%   dPos - the dipole position (3x1) vector
%   m - the (3x1) vector magnetic moment (n*I*A, right-hand rule direction)
%       Note: size(dPos) = size(m)
%   mu - the scalar permeability (default to mu0)
% OUTPUTS
%   bField - the (3XN matrix) Bfield vectors
%   bFieldGradX - the (3XN matrix) gradient vectors of Bfield w.r.t. X
%   bFieldGradY - the (3XN matrix) gradient vectors of Bfield w.r.t. Y
%   bFieldGradZ - the (3XN matrix) gradient vectors of Bfield w.r.t. Z
% ==========================================================================
function [bField,bFieldGradX,bFieldGradY,bFieldGradZ] = ...
        dipoleBField_wDipolePosGradient_SingleDipole(sPos,dPos,m,mu)
    if nargin < 4
        mu = util.Physics.MAGNETIC_CONSTANT;
    end
    if (size(dPos) ~= size(m))
        error ('# dipole Positions must match # dipole orientations')
    end
    % Make r and m have equal size
    if size(sPos,2) < size (m,2) % Impossible for single Dipole function
        sPos = repmat(sPos, 1, size(m,2));
    elseif size(m,2) < size(sPos,2)
        m = repmat(m, 1, size(sPos, 2));
        dPos = repmat(dPos, 1, size(sPos, 2));
    end
    r = sPos - dPos;
    assert (size(r,2) == size(m,2), ...
        'Input r and m must have size in 2nd dim equal to each other or to 1');
%% Compute b field
    rMag = sqrt(sum(r.*r));
    rMag5 = rMag.^5;
    rMag7 = rMag.^7;
    mDotR = sum(m .* r); % 1XN row-vector of magnetic moment dotted with
                         % N radial vectors
    bField = mu/(4*pi)*...
        ( 3*r.*repmat(mDotR./rMag5,3,1) - m.*repmat(rMag,3,1).^(-3) );
%% Compute b field gradient with respect to coordinates X, Y, and Z
    bFieldGradX = -3*mu/(4*pi)*( ...
        r.*(repmat(-5*r(1,:).*mDotR./rMag7 + m (1,:)./rMag5 , 3, 1)) - ...
        - m.*repmat( r(1,:)./rMag5 , 3, 1) + ...
        [mDotR./rMag5; zeros(size(mDotR)); zeros(size(mDotR))] );
    bFieldGradY = -3*mu/(4*pi)*( ...
        r.*(repmat(-5*r(2,:).*mDotR./rMag7 + m(2,:)./rMag5 , 3, 1)) - ...
        - m.*repmat( r(2,:)./rMag5 , 3, 1) + ...
        [zeros(size(mDotR)); mDotR./rMag5; zeros(size(mDotR))] );
```

```
    bFieldGradZ = -3*mu/(4*pi)*( ...
        r.*(repmat(-5*r (3,:).*mDotR./rMag7 + m(3,:)./rMag5 , 3, 1)) – ...
        – m.*repmat( r(3,:)./rMag5 , 3, 1) + ...
        [zeros(size(mDotR)); zeros(size(mDotR)); mDotR./rMag5] );
end
```

The description is provided to enable any person skilled in the art to practice the various embodiments described herein. While various figures and embodiments are referenced, it should be understood that these are for illustration purposes only and should not be taken as limiting the scope of the claims.

There may be many other ways to implement the claimed technology. Various functions and elements described herein may be partitioned differently from those shown without departing from the scope of the subject technology. Various modifications to these embodiments may be readily apparent to those skilled in the art, and generic principles defined herein may be applied to other embodiments. Thus, many changes and modifications may be made to the subject technology, by one having ordinary skill in the art, without departing from the scope of the subject technology.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases A reference to an element in the singular is not intended to mean "one and only one" unless specifically stated, but rather "one or more." The term "some" refers to one or more. Headings and subheadings are used for convenience only, do not limit the subject technology, and are not referred to in connection with the interpretation of the description of the subject technology. All structural and functional equivalents to the elements of the various embodiments described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Implementations of the subject matter and the operations described in this specification can be implemented in digital electronic circuitry, or in computer software embodied on a tangible medium, firmware, or hardware, including the structures disclosed in this specification and their structural equivalents, or in combinations of one or more of them. The subject matter described in this specification can be implemented as one or more computer programs, i.e., one or more modules of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described in this specification can be performed by a data processing apparatus on data stored on one or more computer-readable storage devices or received from other sources.

The terms "data processing apparatus," "computing device," or "processing circuit" encompass all kinds of apparatus, devices, and machines for processing data, including by way of example a programmable processor, a computer, a system on a chip, or multiple ones, a portion of a programmed processor, or combinations of the foregoing. The apparatus can include special purpose logic circuitry, e.g., an FPGA or an ASIC. The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While this specification contains many specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products embodied on tangible media.

References to "or" may be construed as inclusive so that any terms described using "or" may indicate any of a single, more than one, and all of the described terms.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

What is claimed is:

1. A system comprising:
   one or more diamond nitrogen vacancy (DNV) sensors; and
   a controller configured to:
      activate the DNV sensors,
      receive a set of vector measurements from the DNV sensors, and
      determine an angle of a magnetic source relative to the one or more DNV sensors based on the received set of vector measurements from the DNV sensors.

2. The system of claim 1, wherein the magnetic source is a rotating magnetic source.

3. The system of claim 1, wherein the controller is further configured to determine the position and dipole moment of the magnetic source based on the received set of vector measurements from the DNV sensors.

4. The system of claim 3, wherein the angle of the magnetic source relative to the one or more DNV sensors is determined based in part on the determined position and dipole moment of the magnetic source.

5. The system of claim 1, wherein the number of DNV sensors is three or more.

6. A system comprising:
   one or more diamond nitrogen vacancy (DNV) sensors; and
   a controller configured to:
      activate the DNV sensors,
      receive a set of vector measurements from the DNV sensors, and
      determine geolocation of a magnetic source relative to the one or more DNV sensors based on the received set of vector measurements from the DNV sensors.

7. The system of claim 6, wherein the controller is further configured to determine the position and dipole moment of the magnetic source based on the received set of vector measurements from the DNV sensors.

8. The system of claim 7, wherein the geolocation of the magnetic source relative to the one or more DNV sensors is determined based in part on the determined position and dipole moment of the magnetic source.

9. The system of claim 6, wherein the number of DNV sensors is three or more.

10. A geolocating device comprising:
    one or more diamond nitrogen vacancy (DNV) sensors; and a means for activating the DNV sensors, receiving a set of vector measurements from the DNV sensors, and determining an angle of a magnetic source relative to the one or more DNV sensors based on the received set of vector measurements from the DNV sensors.

11. The device of claim 10, wherein the magnetic source is a rotating magnetic source.

12. The device of claim 10, further including a means for determining the position and dipole moment of the magnetic source based on the received set of vector measurements from the DNV sensors.

13. The device of claim 10, wherein the number of DNV sensors is three or more.

14. A system comprising:
one or more diamond nitrogen vacancy (DNV) sensors; and
a controller configured to:
    activate the DNV sensors,
    receive a set of vector measurements from the DNV sensors, and
    determine the position and dipole moment of the magnetic source based on the received set of vector measurements from the DNV sensors.

15. A geolocating device comprising:
one or more diamond nitrogen vacancy (DNV) sensors; and
a means for activating the DNV sensors, receiving a set of vector measurements from the DNV sensors, and determining the position and dipole moment of a magnetic source relative to the one or more DNV sensors based on the received set of vector measurements from the DNV sensors.

16. A system comprising:
one or more magneto-optical defect center sensors; and
a controller configured to:
    activate the magneto-optical defect center sensors,
    receive a set of vector measurements from the magneto-optical defect center sensors, and
    determine geolocation of a magnetic source relative to the one or more magneto-optical defect center sensors based on the received set of vector measurements from the magneto-optical defect center sensors.

17. A geolocating device comprising:
one or more magneto-optical defect center sensors; and
a means for activating the magneto-optical defect center sensors, receiving a set of vector measurements from the magneto-optical defect center sensors, and determining the position and dipole moment of a magnetic source relative to the one or more magneto-optical defect center sensors based on the received set of vector measurements from the magneto-optical defect center sensors.

18. A geolocating device comprising:
one or more magneto-optical defect center sensors; and
a means for activating the magneto-optical defect center sensors, receiving a set of vector measurements from the magneto-optical defect center sensors, and determining an angle of a magnetic source relative to the one or more magneto-optical defect center sensors based on the received set of vector measurements from the magneto-optical defect center sensors.

* * * * *